US012322503B2

(12) United States Patent
Fischer

(10) Patent No.: US 12,322,503 B2
(45) Date of Patent: *Jun. 3, 2025

(54) SYSTEMS, METHODS AND DEVICES FOR ASSET TRACKING

(71) Applicant: Technology Trace Inc., Waterloo (CA)

(72) Inventor: Daniel Michael Fischer, Waterloo (CA)

(73) Assignee: Technology Trace Inc., Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/614,109

(22) Filed: Mar. 22, 2024

(65) Prior Publication Data

US 2024/0274280 A1  Aug. 15, 2024

Related U.S. Application Data

(63) Continuation of application No. 17/409,931, filed on Aug. 24, 2021, now Pat. No. 12,002,574.

(Continued)

(51) Int. Cl.
*G16H 40/20* (2018.01)
*G06K 7/14* (2006.01)
(Continued)

(52) U.S. Cl.
CPC ........... *G16H 40/20* (2018.01); *G06K 7/1413* (2013.01); *G16H 40/40* (2018.01); *G16H 40/67* (2018.01); *H04W 4/029* (2018.02); *G01R 31/382* (2019.01); *G01S 19/14* (2013.01); *G06F 8/65* (2013.01); *G06F 9/54* (2013.01); *H02J 7/0047* (2013.01); *H04W 84/042* (2013.01)

(58) Field of Classification Search
USPC ...... 340/572.1, 525, 539.11, 539.12, 539.13, 340/539.22, 539.28, 557, 588
See application file for complete search history.

(56) References Cited

U.S. PATENT DOCUMENTS 12,002,574 B2 * 6/2024 Fischer ................. G16H 40/40
2006/0279426 A1 * 12/2006 Bonnet ................. A61B 5/1117
340/573.1

(Continued)

*Primary Examiner* — Daniel Previl
(74) *Attorney, Agent, or Firm* — Own Innovation Inc.; James W. Hinton

(57) ABSTRACT

Provided are systems, methods and devices for adaptive and exception-based asset tracking by geolocation, while preserving battery life, ensuring patient privacy and maintaining interoperability by preventing interference with the operation of tracked medical devices. To prevent RF interference with medical device operation, provided are methods of detecting medical device operation through detection of magnetic fields or vibrations. For patient privacy, geolocation information received from an asset tracker device is anonymized and not stored. The asset tracker device described herein may be further configured to track elevation of an asset above the ground, movement of the asset, pressure and temperature changes to the environment and accordingly modify tracking behavior. Also provided is a pairing system for physical and electronic pairing of an asset tracker device to multiple medical devices. The asset tracked is mated with a cradle that is specific to the medical device type and attached to the medical device.

19 Claims, 28 Drawing Sheets

Related U.S. Application Data

(60) Provisional application No. 63/069,450, filed on Aug. 24, 2020.

(51) Int. Cl.
   *G16H 40/40*   (2018.01)
   *G16H 40/67*   (2018.01)
   *H04W 4/029*   (2018.01)
   *G01R 31/382*  (2019.01)
   *G01S 19/14*   (2010.01)
   *G06F 8/65*    (2018.01)
   *G06F 9/54*    (2006.01)
   *H02J 7/00*    (2006.01)
   *H04W 84/04*   (2009.01)

(56) References Cited

U.S. PATENT DOCUMENTS

| | | | |
|---|---|---|---|
| 2011/0054271 A1* | 3/2011 | Derchak | A61B 5/389 |
| | | | 600/595 |
| 2011/0250962 A1* | 10/2011 | Feiner | A63F 13/57 |
| | | | 463/31 |
| 2011/0295110 A1* | 12/2011 | Manzke | G01R 33/287 |
| | | | 600/424 |
| 2014/0257746 A1* | 9/2014 | Dunbar | G01B 7/003 |
| | | | 702/150 |
| 2015/0219732 A1* | 8/2015 | Diamond | A61B 5/0042 |
| | | | 324/201 |
| 2017/0061820 A1* | 3/2017 | Firoozbakhsh | G06Q 20/10 |
| 2019/0167922 A1* | 6/2019 | Cole | A24F 40/48 |
| 2020/0077892 A1* | 3/2020 | Tran | G08B 21/02 |
| 2020/0197099 A1* | 6/2020 | Xu | A61B 34/20 |
| 2020/0383638 A1* | 12/2020 | Shute | A61B 5/6869 |
| 2022/0118240 A1* | 4/2022 | Brand | A61M 39/10 |

* cited by examiner

SYSTEMS, METHODS AND DEVICES FOR ASSET TRACKING

TECHNICAL FIELD

The embodiments disclosed herein relate to asset tracking devices and, in particular to systems, methods and devices for tracking medical devices.

INTRODUCTION

There is an estimated loss of up to $10B per year in North America due to lost or missing medical devices. Due to this financial loss, there is a strong incentive to implement some method of geolocation asset tracking by the owners of these medical devices to minimize financial losses. Most medical devices are owned by the device manufacturer or health institutions but may be taken to a patient's home for use. Thus, there is also a need for systems and methods to allow for robust geolocation asset tracking of medical devices while still maintaining patient privacy.

With respect to patient privacy, a challenge in implementing a geolocation asset tracking system for medical devices is that the patient will need to consent to their personally identifiable information (PII) being collected. While some patients may consent to this tracking of PII, a universal method is required to both collect the geolocation information of the medical device while maintain patient privacy.

Furthermore, what is considered as personally identifiable information is a shifting scale over time as laws change and technology advances. For example, the MAC address of a WiFi router in a patient's home is not considered as personally identifiable information today. However, this MAC address exists in databases of several location analytics companies throughout the world. If this data element is linked to enough consistent identifiers over time, it is within the realm of possibilities that the patient identity can be linked to that MAC address in the future.

Thus, a geolocation asset tracking method for medical devices must ensure that the data stored and collected does not contain any element that could be considered as personally identifiable information today or in the future. Furthermore, measures should be taken to secure and protect the information while in the process of obtaining the geolocation data.

With respect to a secure, robust geolocation of medical devices an asset tracker is required to be able to be re-used for multiple usage tracking cycles over its lifetime and is required to support a simple refurbishment process. The asset tracker device should be also able to support the tracking of different medical device equipment types. Furthermore, to support the simple refurbishment of the asset tracker device, there should be no requirement to strictly pair any medical device with any particular asset tracker device over the various usage cycles for both the asset tracker and the medical device.

A challenge in the asset tracking of medical devices is maintaining awareness of the location of a medical device that is supplied to one or more patients, for variable duration, and under highly variable conditions during a single use cycle. For example, a dialysis machine may be used by a specific patient for several years, given there is no fixed duration for treatment. Similarly, the machine may be kept in storage at a warehouse, hospital, etc., for extended periods of time between uses. Further, the device may be transported and used by several patients in several locations (i.e., a hospital, a high rise, a detached house, etc.) within a single use cycle. Thus, there is no typical usage cycle for a medical device, and that usage cycle will be unique.

To address the variable duration and conditions of the medical device usage cycle, a long battery live is required for an asset tracker. Battery life can be extended by increasing the size of the battery. However, this increases the size, weight, and cost of the battery (and the tracking device). Further, a large battery is counter to the general trend of shrinking medical devices. An asset tracker should be relatively small to allow for it to be widely adopted with medical devices of all sizes.

Another approach to extending battery life, is to set a high static period of communication between the tracking device and an asset management server. The drawback of to this approach is that the static periods may miss events of significance, such as motion, which are important events during the usage cycle of the medical device.

Existing asset tracking systems typically rely on Global Navigation Satellite Systems (GNSS) as the primary geolocation method. In locations that medical devices are typically found such as hospitals and high rises, GNSS will often not be able to obtain a location fix due to their concrete and steel structures and urban locations.

Even asset trackers that use multiple methods for geolocation typically follow a procedure that is non-optimal for battery life. For example, the asset tracker may first try to obtain a geolocation fix using a GNSS receiver, and then timeout, wasting power during this attempt before moving on to another geolocation method.

Another way to extend battery life is to implement control logic or a control system within the asset tracker to optimize the geolocation fix logic. This typically requires floating point operations which would increase the cost of the asset tracking hardware. Furthermore, additional device firmware operations would be required, which themselves consume battery life. This would negate any potential battery savings.

Another consideration is that medical devices must pass a certification requirement and operate within the bounds set by national health regulatory bodies. The Food and Drug Administration (FDA) stipulates a separation distance for external transmitting devices, based on radio frequency (RF) power level.

Currently implemented asset tracking options for medical devices include low power Bluetooth based transmitters and RFID tags. While these devices meet the RF power requirements set by national health regulatory bodies, the fundamental challenge with these class of devices is that they are limited in range and are generally only used in institutions like hospitals.

Existing tracker devices may have directional antennas and RF dampening materials between the cellular radio of the tracker and the medical device. However, this approach is dependent on the orientation of the medical device and tracker relative to a cellular base station, which will be highly variable.

A possible solution to meet the RF energy requirement would be to tether an asset tracker at a suitable distance from the medical device. However in practice, this may be fraught with difficulties, for example, relying on the patient to ensure the tracker is suitably far away. Also, improper placement of the tracker may result in electromagnetic interference to the medical device, and may impact therapy delivery.

Accordingly, there is a need for robust and improved tracking systems, methods and devices for the adaptive tracking of, and interoperability with, medical devices, and other physical assets, for variable duration and across variable conditions.

SUMMARY

Provided is an asset tracking system, comprising an asset tracker device, configured to record one or more readings from one or more sensors, determine an operational state based on the one or more sensor readings, perform a scan to obtain a geolocation position fix, wherein the scan is performed during a heuristic window coinciding with the operational state when a therapy is not provided, communicate the one or more sensor readings and the anonymized geolocation position fix to a backend system over a cellular network during the heuristic window, receive a response from the backend system during the heuristic window; and optimize battery usage of the asset tracker device according to the response.

The system may further include a cradle having a dock for receiving the asset tracker device, wherein, the cradle is fixed to an external surface of the asset via an adhesive or clamping mechanism; and a tamper proof fastener for removably attaching the asset tracker device to the cradle.

The one or more sensors may include any one or more of a magnetometer, an inertial measurement unit, a barometric pressure sensor; and a temperature sensor.

The geolocation position fix may include any one or more of a latitude and a longitude, a WiFi access point MAC address, a cellular base station ID, and a location area code.

The asset tracker may be configured to adjust the heuristic window based on the one or more sensor readings.

The cradle may be fixed to the asset by an adhesive or through a mechanical clamping mechanism.

The asset may be a medical device.

The medical device may be an Automated Peritoneal Dialysis Unit or a Hemo Dialysis Unit.

The backend system may be configured to receive the anonymized geolocation position fix and the one or more sensor readings over the cellular network, from the asset tracker device, store the one or more sensor readings in a database, and communicate the response to the asset tracker device.

The backend system may be configured to calculate an estimated battery life for the asset tracker device based on the one or more sensor readings, and set one or more control parameters based on the estimated battery life, wherein the response includes the one or more control parameters.

The backend system may be configured to set or steer the operational state of the asset tracker device based on one or more sensor readings, or external conditions, and set one or more control parameters based on the operational state, wherein the response includes the one or more control parameters.

The backend system may be configured to optimize one or more control parameters in a feedback control loop having regard to a plurality of reference parameters.

The backend system may be configured to communicate the geolocation position fix to an API service, and receive the response from the API service.

The API service response comprises anonymized location data based on the geolocation position fix and a Point of interest ID, and may also include estimated elevation above ground, local weather conditions including a current temperature and a sea level barometric pressure.

Provided is a method for tracking medical assets to maintain interoperability with the medical asset, avoid interference with therapy delivery and maintain patient privacy. The method includes pairing an asset tracker device to a medical device, recording one or more readings from one or more sensors in the asset tracker device, sensing an operational state of the medical device by detecting a magnetic field or vibration from the medical device, performing a scheduled geolocation position scan within a heuristic window to obtain a geolocation position fix, wherein the heuristic window coincides with the medical device not in operation, and obtaining anonymized location data from the geolocation position fix.

The method may future include assessing whether the scheduled geolocation position scan occurs within the heuristic window, and adjusting the scheduled geolocation position scan to occur within the heuristic window.

The method may further include setting one or more control parameters to optimize battery usage of the asset tracker device, based on the one or more sensor readings.

Provided is a non-transitory computer-readable storage medium having stored thereon computer-executable instructions that, when executed by a processor of an asset tracker device, cause an asset tracker device to awake from a low-power state, record one or more readings from one or more sensors, determine an operational state of the asset tracker device based on the one or more readings, assess whether a present time coincides with a heuristic window for performing one or more geolocation positioning scans, and return to the low-power state when the present time is not within the heuristic window.

The non-transitory computer-readable storage medium may further comprising instructions to perform the one or more geolocation positioning scans to obtain a geolocation position fix, wherein the one or more geolocation positioning scans comprise a global navigation satellite scan, a WiFi access point scan, wherein the WiFi access point scan is performed when the geolocation fix is not obtained by the global navigation satellite scan, and a cellular base station triangulation scan, wherein the cellular base station triangulation scan is performed when the geolocation fix is not obtained by the WiFi access point scan, record a successful scan type, and perform a subsequent geolocation position scan commencing with the successful scan type.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings.

DETAILED DESCRIPTION

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, cloud-based program or system, or asset tracker device.

Each program is preferably implemented in a high-level procedural or object-oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

A description of an embodiment with several components in communication with each other does not imply that all such components are required. On the contrary a variety of optional components are described to illustrate the wide variety of possible embodiments of the present invention.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

Figure 1A:
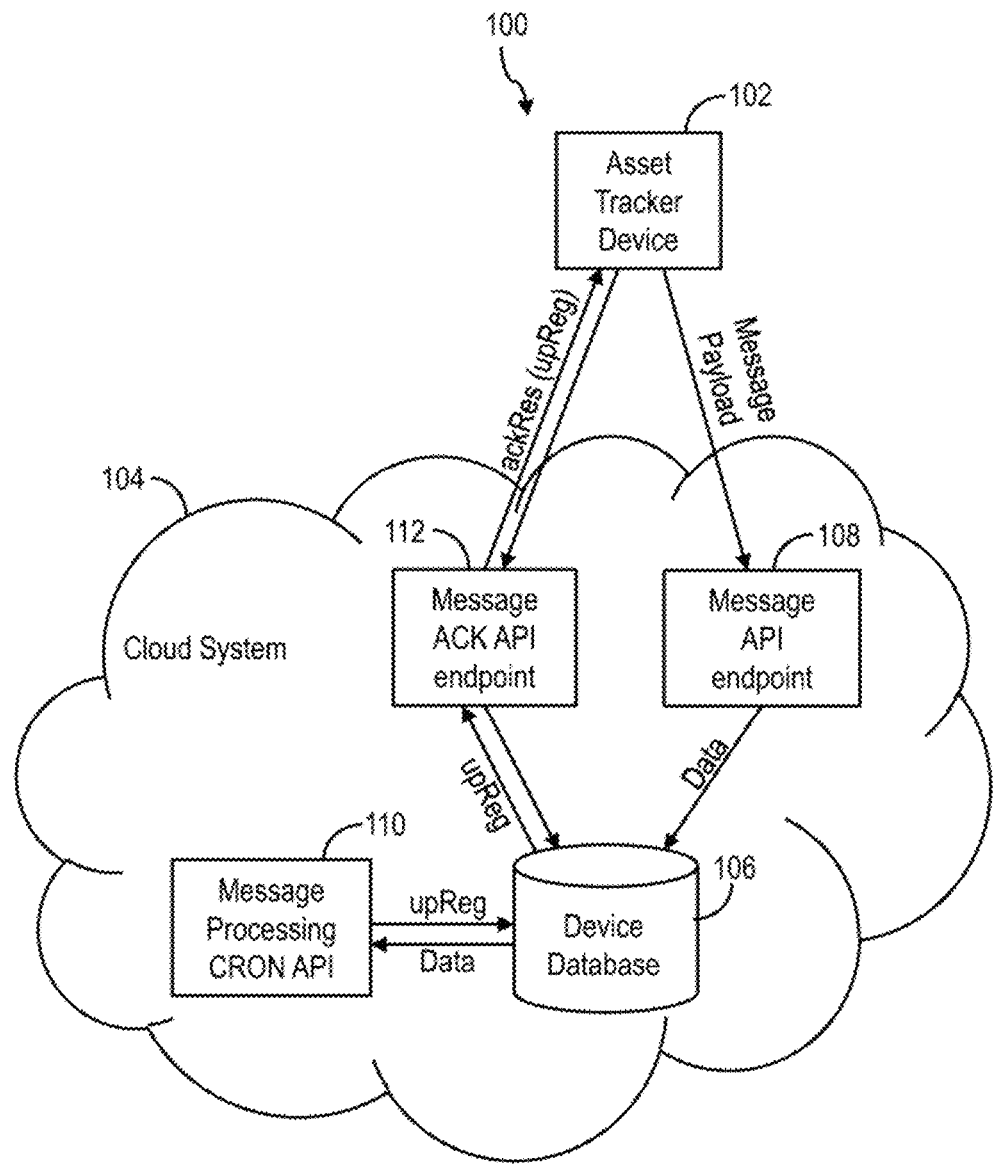
FIG. 1A is a diagram of a location position system (LPS) messaging system, according to an embodiment.

Referring to FIG. 1A, illustrated therein is a diagram of a location position system (LPS) messaging system 100, according to an embodiment. The system 100 includes an IoT asset tracker device 102. The asset tracker device 102 is attached to a medical device, for tracking the location of the medical device during its operation in the field. According to an embodiment, the messaging system 100 may include a plurality of asset tracking devices, wherein each asset tracker device is attached to a medical device.

The messaging system 100 includes a backend cloud system 104. The cloud system 104 may be hosted by one or more servers. The cloud system 104 includes at least one database 106 for storing data messages received from the asset tracker device 102. The asset tracker device 102 is connected to the cloud system 104 over a cellular (mobile) communications network.

The cloud system 104 includes a plurality of virtual machines that process function APIs. The cloud system 104 includes a message API endpoint 108 configured for receiving messages from the asset tracker device 102 and storing the messages in a queue for processing by the cloud system 104.

Inside the asset tracker device 102, a controller initiates a geo-location position scan at a defined period and collects sensor data of the device and its environment. A data message is then constructed based on various measured and calculated elements such as geolocation information, time elements and battery State of Charge. This message is then communicated to the message API endpoint 108 in the cloud system 104 via the asset tracker device's cellular radio.

The cloud system 104 includes a CRON-based message ingestion function API, message processing CRON API 110. The message processing CRON API 110 is configured to read each new data message in the queue, process the data, and determine an updated battery life prediction for the tracker device that sent the data message. The message processing CRON API 110 also processes other information from the database 106 to construct an update register value ("upReg" in FIG. 1A) used to control and modify the tracker device's behavior and actions.

The cloud system 102 includes a message acknowledgement API endpoint (message ACK API endpoint 112). The message ACK API endpoint 112 is configured to confirm successful receipt of the data message by the cloud system 104 by returning an acknowledge response register value ("ackRes" in FIG. 1A). The acknowledge response register value includes confirmation of successful message receipt by the cloud system 104, and the update register value. The update register value is decomposed on the tracker device in the asset tracker device 102, and the device's configuration and behavior is modified based on the feedback from the cloud system 104. Exemplary operations of the messaging system 100 are described in detail below with reference to FIGS. 4A-4B.

Figure 1B:
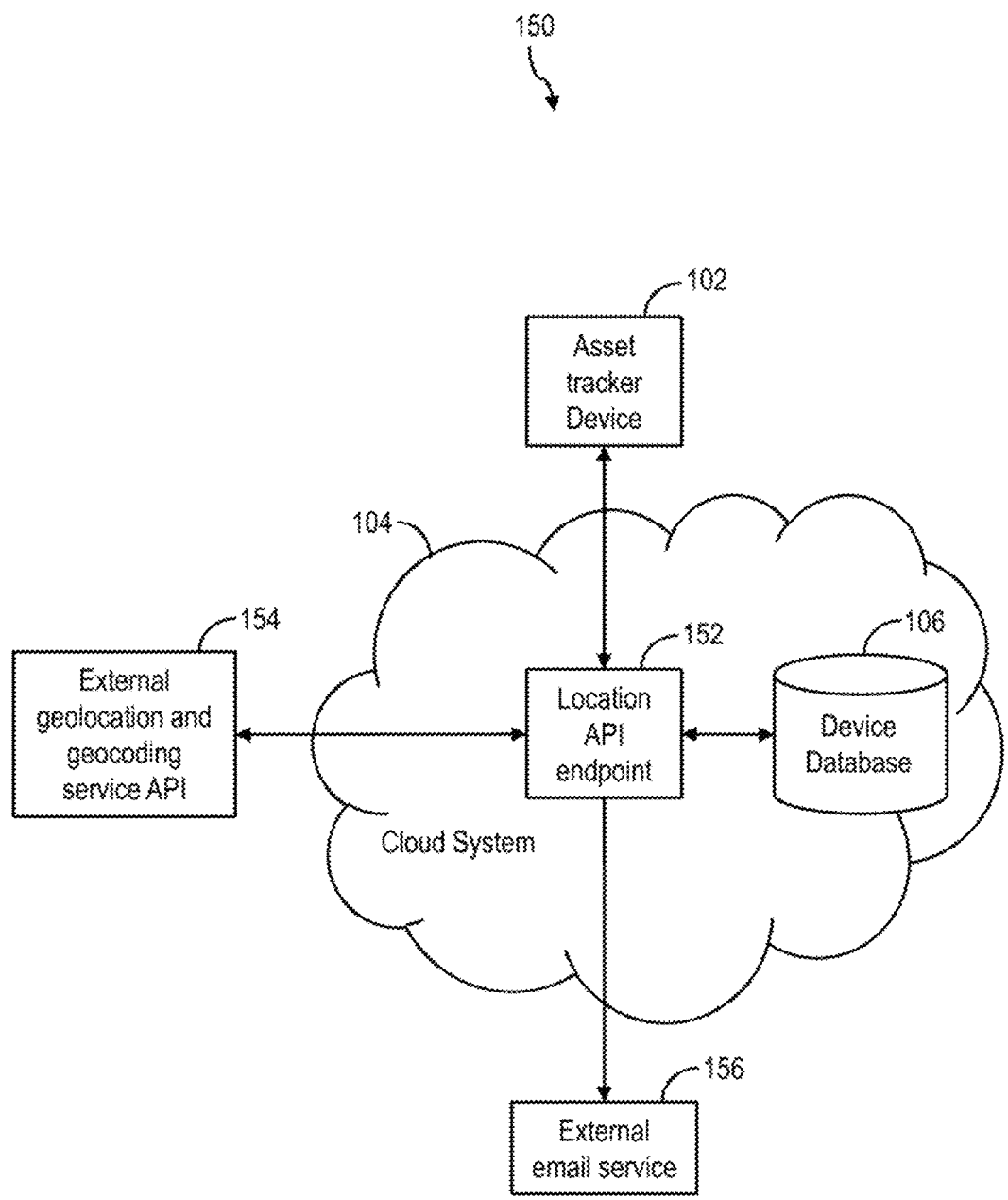
FIG. 1B is a diagram of a distributed anonymized geolocation asset tracking system, according to an embodiment.

Referring to FIG. 1B, illustrated therein is a diagram of a distributed anonymized geolocation asset tracking system 150, according to an embodiment. The asset tracking system 150 shares common elements with the LPS messaging system 100 in FIG. 1A, including, the asset tracker device 102, the cloud system 104 and database 106. The systems 100, 150 may be the same system, and are shown here separately for ease of illustration and explanation.

The asset tracker device 102 is connected to the cloud system 104 over a cellular (mobile) communications network. The cloud system 104 includes a location API endpoint 152. The location API endpoint is connected to the tracker device 102 by a secure encrypted channel. The location API endpoint 152 is configured to receive the encrypted geolocation message, store it into a RAM, decode the asset tracker device serial number from the location message payload and parse and construct an external message for an external geocoding service API 154 and return anonymized location data back to the tracker device.

The external geocoding service API 154 returns full geolocation information including latitude, longitude, error; location address including street number, street name, city, state/province, country and ZIP/postal code. The asset tracking system 150 includes an external email service 156 for alerting relevant parties if the tracker device 102 is flagged as lost or stolen. Exemplary operations of the asset tracking system 150 are described in detail below with reference to FIGS. 3A-3D.

Figure 1C:
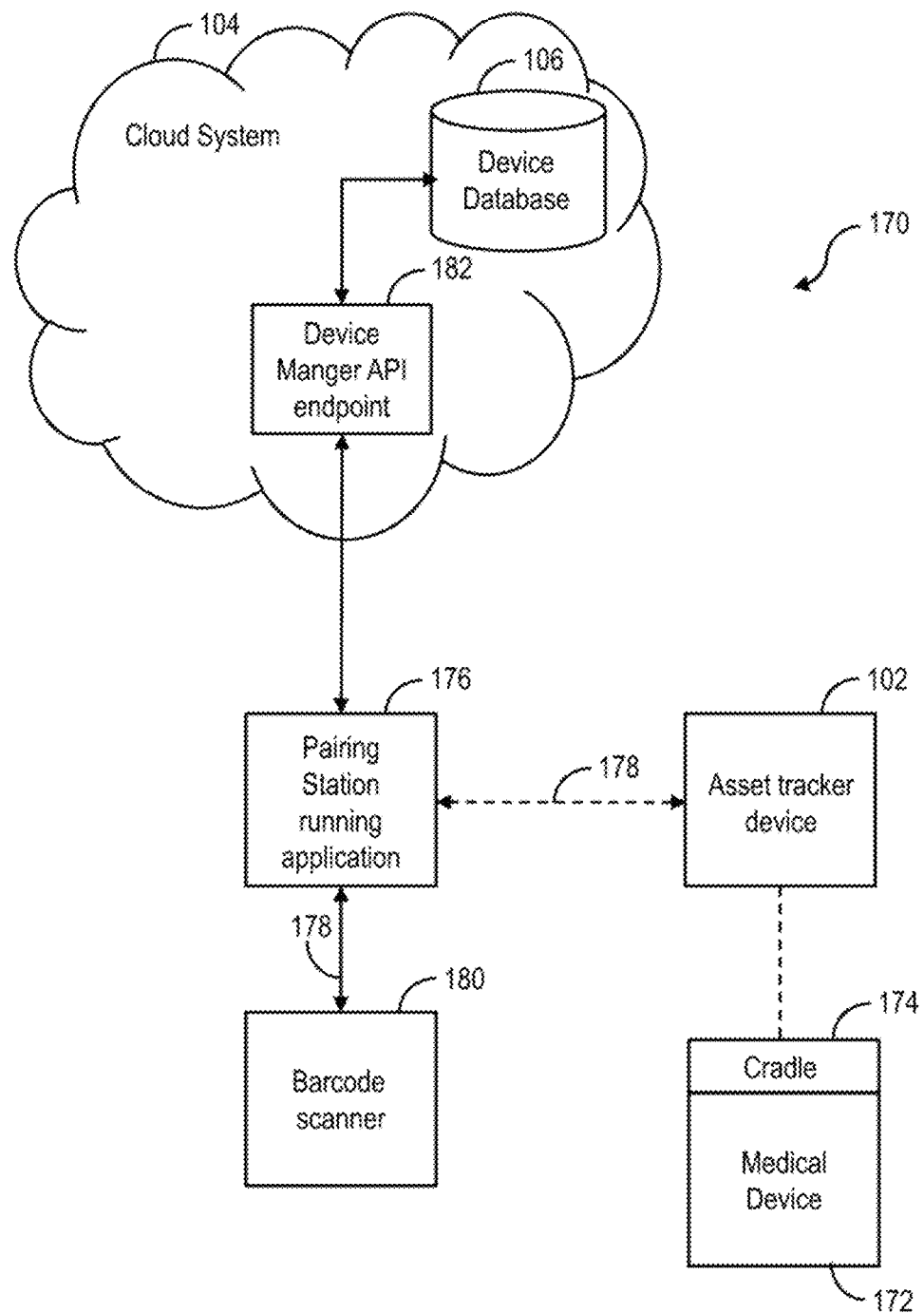
FIG. 1C is a diagram of a pairing system 170, according to an embodiment.

Referring to FIG. 1C, illustrated therein is a diagram of a pairing system 170, according to an embodiment. The pairing system 170 may be used to physically and electronically pair an asset tracked device 102 and a medical device 172. The pairing system 170 shares common elements with the LPS messaging system 100 in FIG. 1A and the distributed asset tracking system 150 in FIG. 1B, including, the asset tracker device 102, the cloud system 104 and database 106. The systems 100, 150, 170 may be the same system, and are shown here separately for ease of illustration and explanation.

The pairing system 170 includes a cradle 174. During physical pairing, the asset tracker 102 is mated to the cradle 174 as described below with reference to FIGS. 2A-2E. The mounting of the cradle 174 to the medical device 172 is unique for each medical device type, accommodating the physical geometry of the medical device 172. The cradle 174 is attached to the medical device 172 without any permanent alteration to the medical device 172. The cradle 174 may be attached to the medical device 172 by, for example, double sided adhesive.

The pairing system 170 includes a pairing station 176 running a pairing application. The pairing station 176 may be computer, tablet, etc. The pairing station 176 is connected to the cloud system 104 over the internet. The tracker device 102 may be connected to the pairing station 176 by a USB interface 178. Communication between the tracker device 102 and the pairing system can be achieved directly through the USB wired communication link 178 or wirelessly through the device manager API endpoint 182, which leverages the cloud system 104 to communicate to the tracker device 102.

When the tracker device 102 is connected to the pairing station 176, the pairing application is configured to make one or more changes to the tracker device 102, for example: whitelisting and pairing; enumeration and unpairing; a firmware update; an update to encryption keys; a diagnostic self-test; or charge battery.

The same pairing station 176 may be used to both pair and unpair the asset tracker device 102 and the medical device 172; alternatively, a first pairing station at a first location may be used for unpairing, and a second pairing station at a second location may be used for pairing.

The pairing system 170 includes a barcode scanner 180 for scanning a barcode on the medical device 172. The barcode scanner 180 is connected to the pairing station 176 via a USB interface 178. Barcodes read by the scanner 180 are received by the pairing application running on the pairing station 176 for electronic pairing of the tracker device 102 to the medical device 172.

The pairing system 170 includes a device manager API endpoint 182 connected to the pairing application running on the pairing station 176 over a communications network. The device manager API endpoint is configured to receive a tracker device serial number as scanned by the barcode scanner 180 from the medical device 172. The device manager API 182 is further configured to check the database 106 whether the asset tracker device 102 is whitelisted and running the latest firmware.

The pairing system 170 may be used to physically and electronically pair an asset tracker 102 to a medical device 172 (or generally, to any asset) for tracking. Physical pairing achieved by mating the asset tracker device 102 with the cradle 174 attached to the medical device 172. Electronic pairing is based on a pairing key. The pairing key is a unique identifier and may be a 12-digit hexadecimal number with the format:

pairingKey=0xSSSSSSSSNNNN where 0xSSSSSSSS is a unique hex 8-digit asset tracker device serial number that is assigned at time of device manufacture and 0xNNNN is the unique hex 4-digit cycle count value that reflects the current asset tracking cycle of the tracker device 102. For example, a tracker device 102 with serial number 0x2468ABCD and its fifth asset tracking cycle would have the cycle count value be equal to 0x0005 and the pairing key would be 0x2468ABCD0005.

Within the database 106, the pairing key is tied to both the specific medical device 172 serial number and all information and data pertaining to that asset tracking device 102 usage cycle such as geolocation data, alert data, device data, etc. Therefore, the pairing key allows all information about the medical device 172 usage cycle to be logically grouped.

The device tracking cycle starts once the asset tracker device 102 is both physically and electronically paired to a new medical device 172. The device tracking cycle ends once the asset tracker device 102 is physically unpaired, i.e. the tracker device 102 is physically removed from the cradle 174, and electronically unpaired from the medical device 172.

When the asset tracker device 102 is subsequently paired with a new medical device 172, the tracker device 102 cycle count value increments by one. For example, given the exemplary device with serial number 0x2468ABCD, it will complete its fifth tracking cycle when it is unpaired from a medical device 172. When the tracker device 102 is next used and electronically and physically paired to another medical device 172, its cycle count would be equal to 0x0006 and the new pairing key would be 0x2468ABCD0006.

An advantage of the pairing system 170 is the flexibility of the given asset tracker device 102 to be able to track an unlimited number of different medical devices 172 by attaching to the cradle 174 that is specific to each medical device type (or asset type, generally). Thus, there is no fixed one-to-one correspondence between a particular medical device 172 (or a particular asset, generally) and a given asset tracker device 102. Thus, the pairing system 170 maintains a common asset tracker device 102 form factor, software and firmware for tracking different medical device types.

A further advantage is the pairing system 170 is secured by leveraging whitelisting and blacklisting. Whitelisting refers to the notion of being authorized; blacklisting refers to the notion of being unauthorized. Through operation of the pairing system 170 a device's whitelisting status is continually confirmed through every contact with the cloud system 104 and the pairing application 176.

The pairing application on pairing station 176 is also whitelisted against each installation instance to prevent against improper duplication. A security key is provided to authorized personnel for each installation instance to allow for loading onto a new desktop computer (i.e., a new pairing station 176). Once installed, the desktop application software retrieves hardware identifiers of the desktop computer binding these identifiers to the supplied security key. This binding of security key and computer hardware identifier is then stored in the cloud system 104 for further authentication when the pairing application is initialized on each subsequent startup to prevent against improper duplication of the pairing application.

In this manner, tracker device and pairing application whitelisting is to be used in the system 170 to ensure only authorized tracker devices 102 connect to the cloud system 104 the pairing application. If a non-white listed device communicates to either the cloud system 102 or the pairing station 176, a message will be sent back that will cause the unauthorized device to eliminate its memory contents and load a blank application that will render the unauthorized device non-functional. Exemplary operations of the pairing system 170 are described in detail below with reference to FIGS. 7A-7D.

Figure 2A:
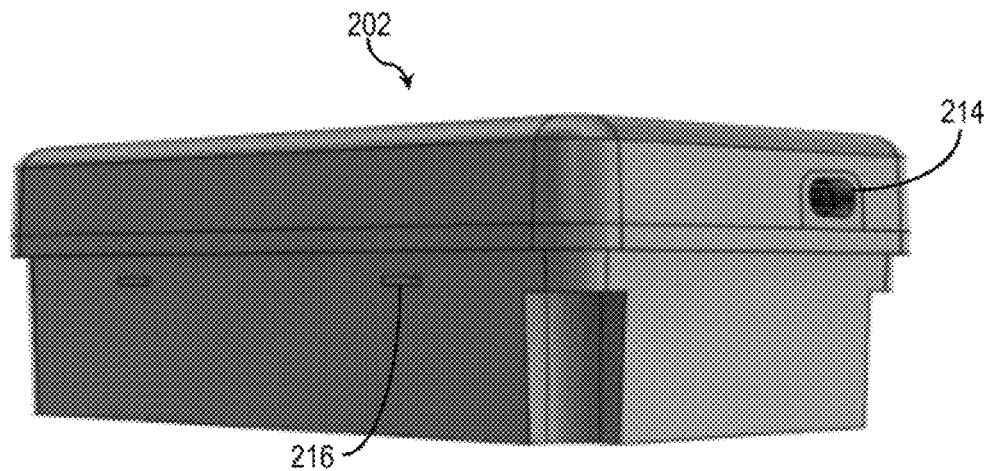
FIGS. 2A-2B are a side perspective and a front perspective view, respectively, of an asset tracker device, according to an embodiment.
Figure 2B:
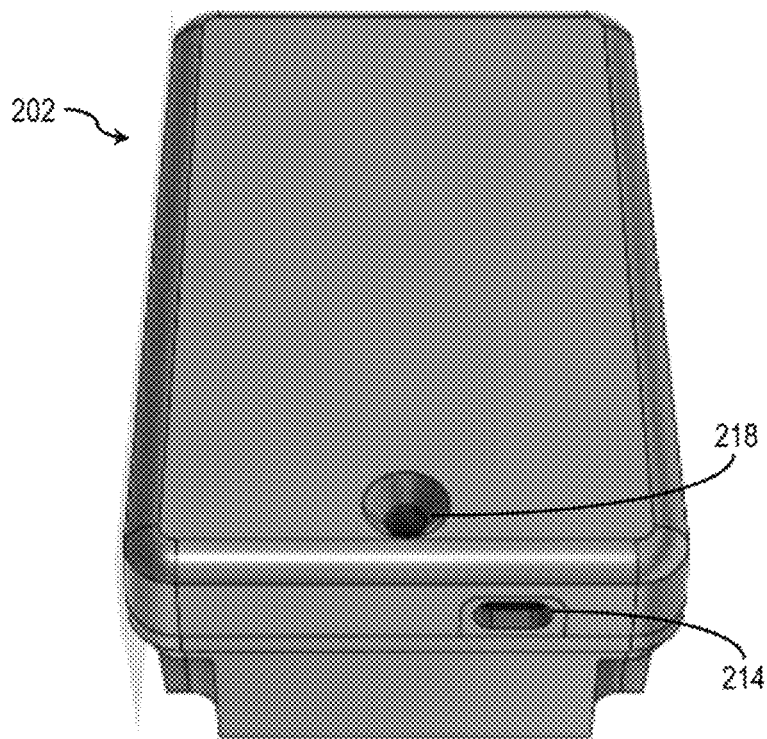

Referring to FIGS. 2A-2B, illustrated therein is side and front perspective views, respectively, of the asset tracker device 202, according to an embodiment. The asset tracker device 202 may be the tracker device 102 in FIGS. 1A-1C. The asset tracker 202 includes an aperture 218 for receiving a tamper proof fastener (not shown). The asset tracker 202 includes a USB port 214 through which data may be exchanged with a pairing station application and through which power is supplied to recharge the device's internal battery. The asset tracker 202 may include one or more protrusions 216.

Figure 2C:
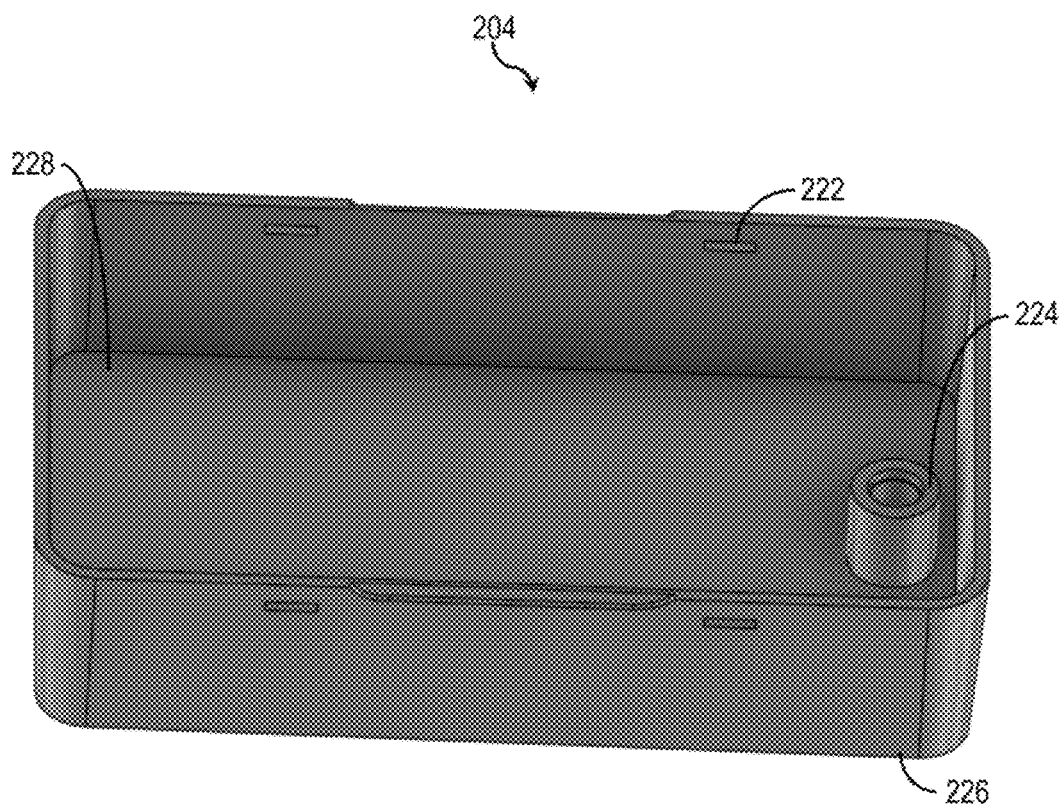
FIG. 2C is a perspective view of a cradle, according to an embodiment.

Referring to FIG. 2C illustrated therein is the cradle 204, according to an embodiment. The cradle 204 may be cradle 174 in FIG. 1C. The cradle 204 includes a screw insert 224 for receiving a tamper proof fastener. The cradle 204 includes one or more recesses 222 for receiving the protrusions 216 on the asset tracker 202 to allow the asset tracker 202 to be oriented correctly with respect to the cradle 204. The cradle 228 includes a dock 228. The dock 228 is shaped to mate with the asset tracker device 202, such that the asset tracker 202 is substantially held within the dock 228 when paired.

The cradle 204 includes a mounting surface 226 for attaching the cradle 204 to the medical device. The mounting surface 226 may shaped to conform to an external surface of the medical device. The mounting surface 226 may include structural features (e.g., grooves, flanges, etc.) to ensure consistent placement onto the medical device is achieved. For example, for some medical devices containing posts/poles, the mounting surface 226 include a clamping mechanism with screws to attached to the posts/poles on the medical device. An advantage of this approach is that with the use of a relatively cost cradle 204 for each medical device type, a common asset tracker device design can service multiple different types of medical assets.

Figure 2D:
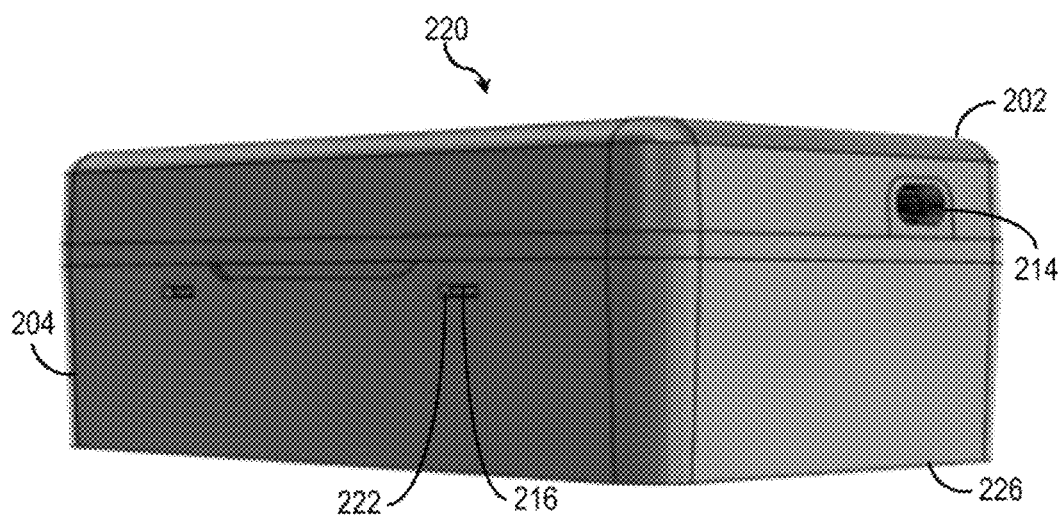
FIGS. 2D-2E are a side perspective and a front perspective view, respectively, of a paired asset tracker device and cradle, according to an embodiment.
Figure 2E:
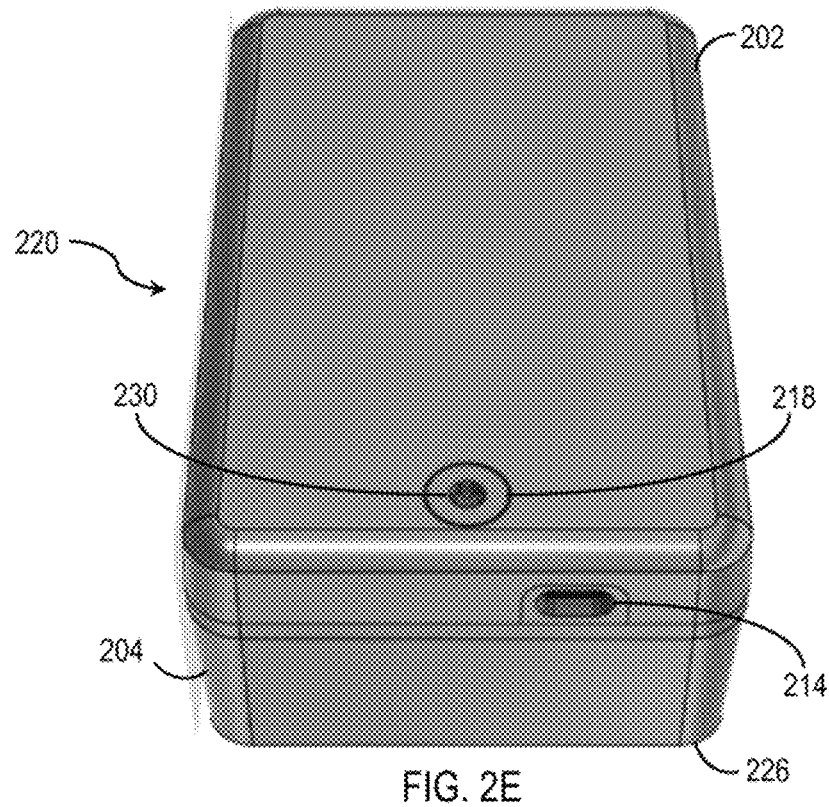

Referring to FIGS. 2D-2E, illustrated therein is side and front perspective views, respectively, of a paired asset tracker 220, according to an embodiment. The paired asset tracker 220 includes the asset tracker device 202 mated to the cradle 204. When mated, the projections 216 on the asset tracker device 202 are received into the recesses 222 on the cradle 204.

To securely hold the asset tracker device 202 to the cradle 204 (and the medical device), the aperture 218 is aligned with the screw insert (not shown) in the cradle 204, and a tamper proof fastener 230 is passed through the aperture 218 to engage the nut. The tamper proof fastener 230 holds the paired asset tracker 220 in place for the duration of the asset tracking cycle. Once the medical device asset is returned for refurbishment, the tamper proof fastener 230 is removed, and the device 202 is removed from the cradle 204, i.e., physical unpairing.

Figure 2F:
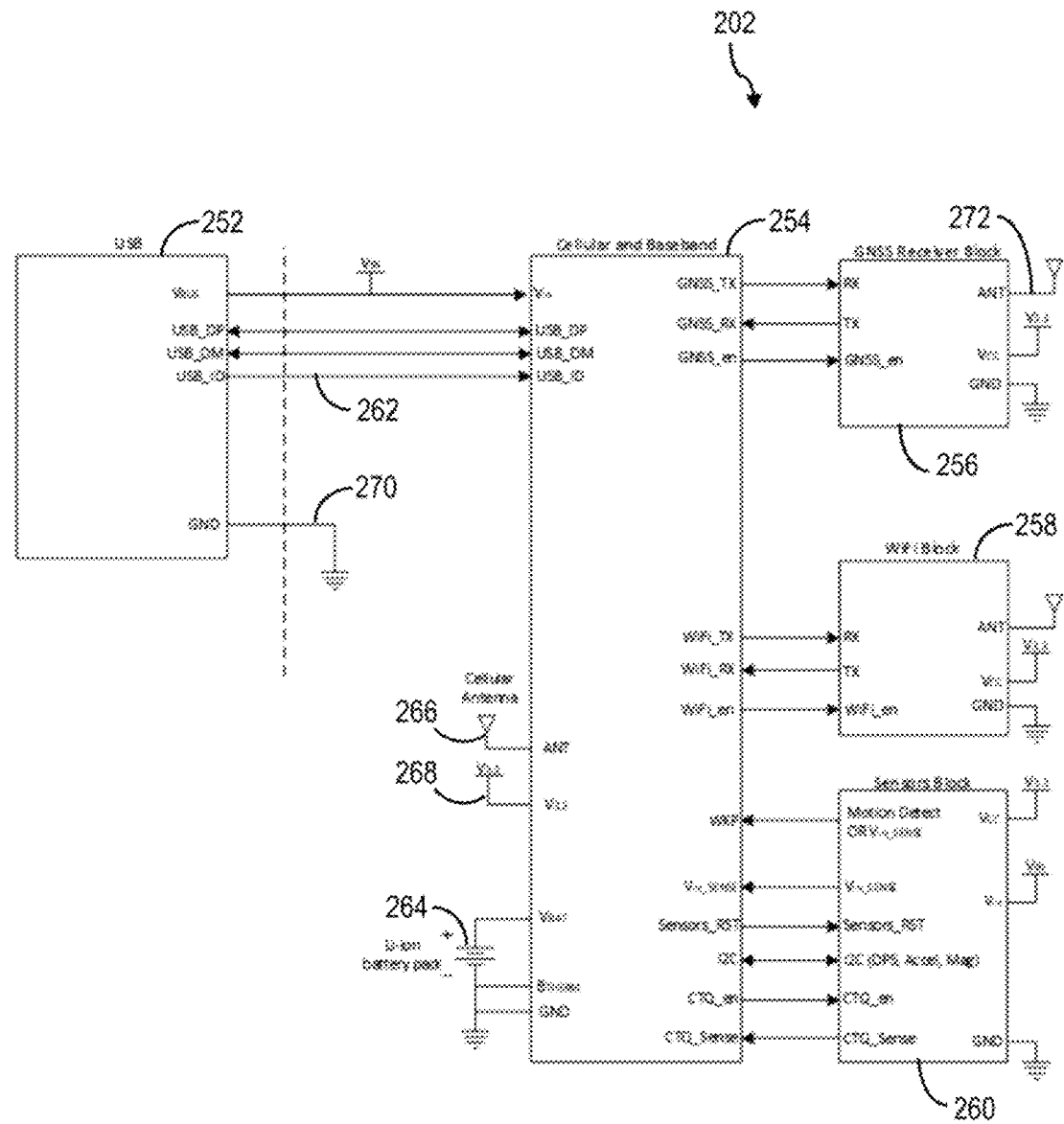
FIG. 2F is a schematic diagram of the components of an asset tracker device, according to an embodiment.

Referring now to FIG. 2F, illustrated therein is a schematic diagram of the components of the asset tracker device 202 shown in relation to a pairing station 252, according to an embodiment. The asset tracker device 202 includes a plurality of components for performing LPS operations and sensing the environment around the device 202.

The asset tracker device 202 includes a USB module for connecting the asset tracker 202 to the pairing station 252 for pairing and unpairing the asset tracker 202 from a medical device. The pairing station 252 includes a USB communication interface. Charging of the device 202 battery 264 is completed over the USB interface only when connected to the pairing station 252 running the pairing system application via the USB port (i.e., USB port 214 in FIGS. 2A-2B).

Charging of the battery 264 is further restricted until both a hardware and software enumeration are completed as described below with reference to FIGS. 7C-7D. Hardware enumeration is performed using a special USB cable 262 where the USB-ID line is connected to the ground line in the USB-B connector. The software enumeration is completed by the pairing application, which sends an enumeration signal to the device 202, which is a key known only to the device and the cloud system. Once the hardware and software enumeration are completed, the device 202 enables charging from a device power management integrated circuit (PMIC) and battery recharging can commence. This approach precludes battery charging in non-authorized and non-controlled situations.

The asset tracker 202 includes a cellular and baseband module 254 for connecting the asset tracker 202 to a cellular (wireless) communications network and receive and transmit data over the network. The cellular module 254 includes a cellular modem, a real time (epoch time) clock, a cellular antenna 266, a microcontroller with multiple GPIOs and communication interfaces (UART, I2C, SPI), SRAM flash memory, the PMIC and fuel gauge for managing battery charging and operation, and a 3.3V power supply 268, which is fed to power the rest of the device 202 components. When the pairing station 252 connected to the device 202, a general-purpose input/output (GPIO) of the microcontroller (which is connected to 3.3V through a pull-up resistor) is driven low. The GPIO line 262 going low completes the hardware enumeration. Once the hardware and software enumeration is completed by the pairing station 252, the device 202 turns on the cellular radio 266 and connects to the cloud system.

The asset tracker 202 includes a GNSS receiver block 256 for establishing a geolocation fix with GNSS satellites. The GNSS block 256 includes a receiver, low noise amplifier (LNA), an active antenna 272, a UART serial communication interface, a real time clock (RTC) to allow for timing reference for the receiver, and a hardware backup mode. The hardware backup mode allows for data to be saved in the GNSS receiver's backup SRAM to allow for hot/warm starts while removing power to the rest of the GNSS receiver subsystem. The hardware backup mode is powered through the device's 3.3V power rail. Power to the rest of the GNSS receiver system is powered through a load switch, whose input is from the 3.3V supply 268 from the cellular module 254. The load switch can then be used to eliminate all load from the GNSS block 272 excluding the backup mode when not in use. Power to the GNSS receiver block 272 can be enabled through a GPIO from the device's microcontroller. A pull-down resistor is present on this enable line to ensure that the GNSS block 272 remains unpowered when not in use.

The asset tracker 202 includes a WiFi transceiver 258 for connecting the asset tracker 200 to a WiFi network and sending and receiving data over the WiFi network. The WiFi block 258 includes a WiFi radio, an antenna, an embedded microcontroller, and a UART serial communication interface. Power to the WiFi radio system is powered through a load switch, whose input is from the 3.3V supply 268 from the cellular module 254. The load switch can then be used to eliminate all load from the WiFi block 258 when not in use. Power to the WiFi block 258 can be enabled through a GPIO from the device's microcontroller. A pull-down resistor is present on this enable line to ensure that the WiFi block 258 remains unpowered when not in use.

The asset tracker 202 includes a sensors block 260 having a plurality of sensors for detecting the environment around the asset tracker 202. The sensors 260 include a magnetometer, a pressure sensor and an inertial measurement unit (IMU). According to an embodiment, the sensors block 260 may include a temperature sensor and/or a barometric pressure sensor. Each sensor is an integrated circuit that communicate with the device microcontroller over an I2C communication interface. Additionally, power to the sensor block 260 is provided through a load switch, whose input is from the 3.3V supply 268 from the cellular module 254. The load-switch is normally kept on. Power to the sensors block 160 can be cycled to achieve a full reset or removed to go into a further lower power state.

Referring back to FIGS. 1A-1B, an advantage of the systems 100, 150 is that computing and processing power can be distributed to the cloud system 104, allowing for a reduction of computing and firmware complexity for the asset tracker device 102, while allowing for higher levels of complex CPU operations to be implemented on the cloud system 104. This distributed control system approach allows for a simpler, lower cost and a lower power device implementation and ultimately saving battery life and extended battery life in a small form factor is achieved, due to constant optimization processes as described below.

A further advantage of the systems 100, 150 is that the asset tracking device 102 can behave in a more efficient exception-based management approach for transmission of data to the cloud system 104 based on important events such as change in location, drop impact events, recalls, or even due to environmental condition changes of the medical device, or asset, being tracked. Thus, the behavior of the asset tracker device 102 can be dynamically modified through the device's unique conditions thereby individually optimizing device performance for such factors as battery life. Additionally, this dynamic and adaptive behavior modification would allow for smaller battery pack capacities, which can lead to smaller device form factors. The optimization of performance and exception-based management approach is achieved by modelling the messaging system 100 as a feedback control system.

Figure 1D:
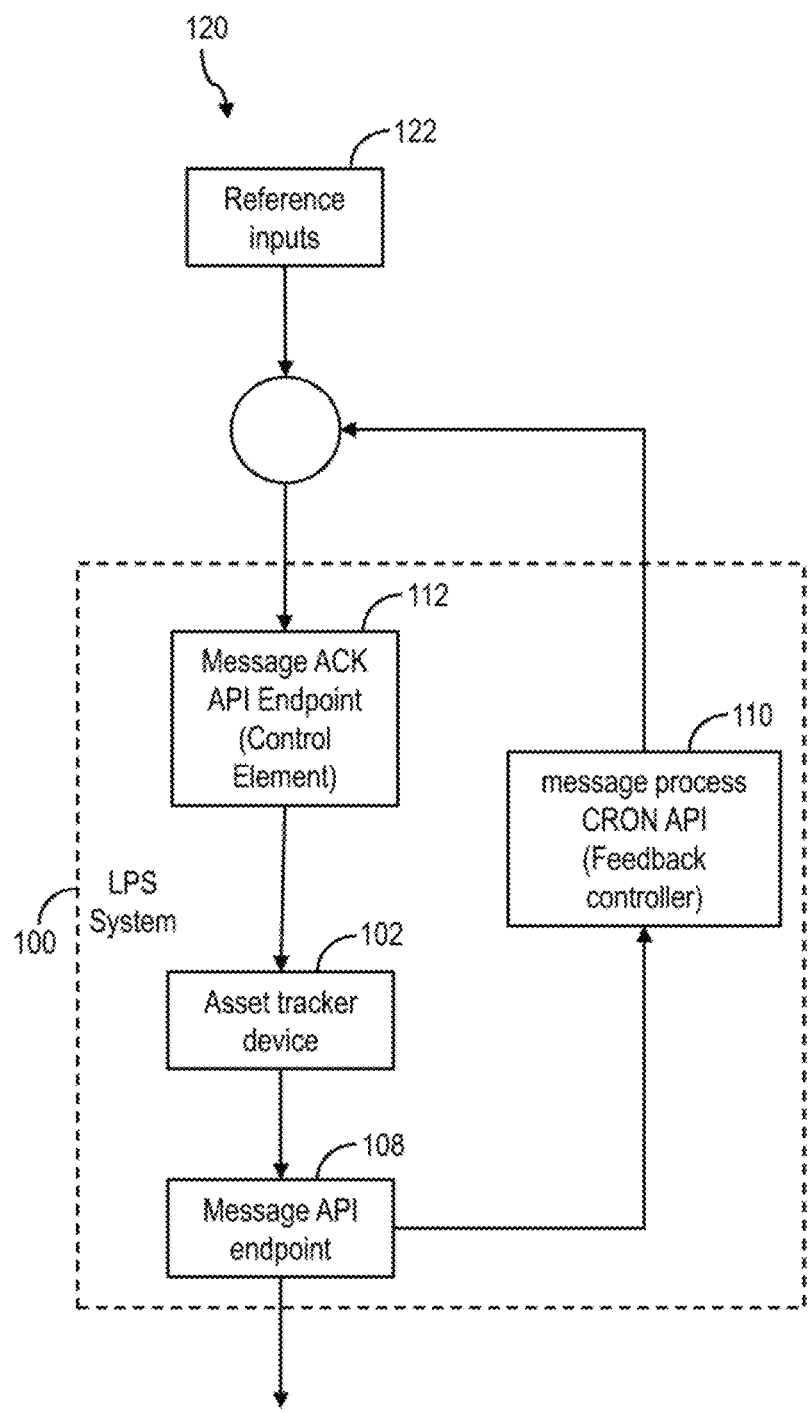
FIG. 1D is a diagram of an adaptive feedback control model of the asset tracking system in FIG. 1A.

Now referring to FIG. 1D, illustrated therein is a diagram of an adaptive feedback control model 120 of the LPS messaging system 100 in FIG. 1A. The distributed nature of the system 100 allows for a high level of mathematical operational complexity to be achieved with only small impact to the battery life of the device 102.

From control system theory, a mathematical model of any system is an approximation towards the dynamic behavior of the system. Additionally, there are no exact models of real systems. Furthermore, we can assume that these systems are non-linear in nature. One approach to modeling the feedback control system 120 would be to use the following non-linear discrete time state-space system as follows:

$$x_k = F(x_{k-1}) + \eta_k \qquad (1)$$

$$y_k = G(x_k) + v_k \qquad (2)$$

where $x_k$ is the system state vector at time step k, $y_k$ is the output measurement vector, $F(x)$ is the process model, and $G(x)$ is the output measurement model, $\eta_k$ is the disturbance noise vector and of zero mean Gaussian noise with covariance $Q_k$ and $v_k$ is the measurement noise vector also of zero mean Gaussian noise with covariance $R_k$.

Using this mathematical model and approach will allow for predicting the outputs of the LPS messaging system 100 given known initial conditions and known reference inputs 122. To optimize for battery life, the mathematical model was constructed by conceiving a coulomb or energy consumption model.

Figure 1E:
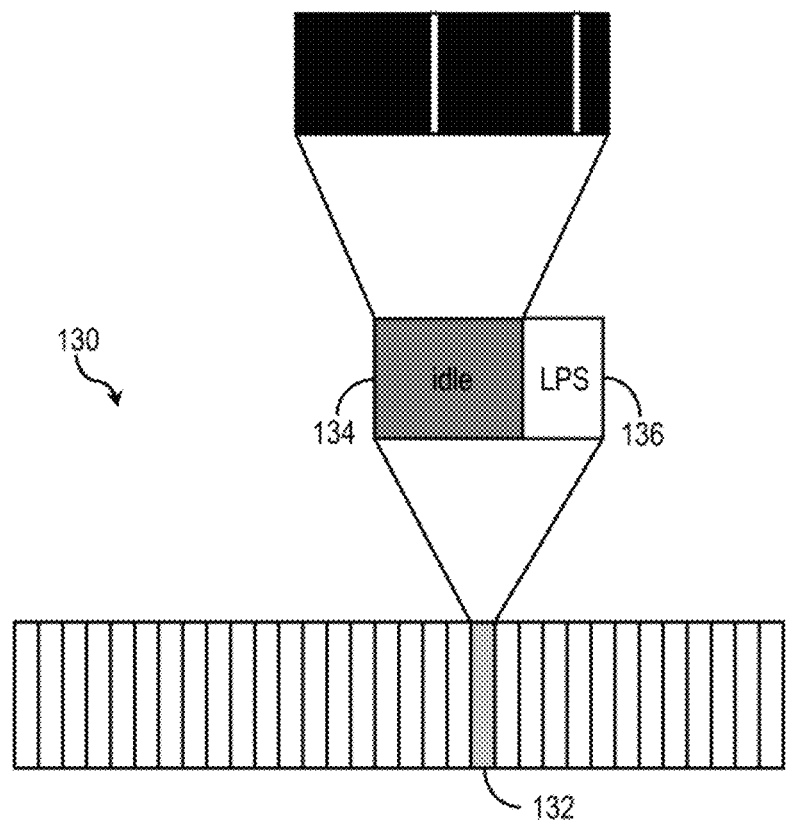
FIG. 1E is a diagram of set of operation cycles for an asset tracked device, according to an embodiment.

The general operation of the asset tracker device 102 can be conceived as a set of operation cycles 130 as shown in FIG. 1E. An operation cycle 132 contains an idle period 134 and an LPS operation period 136. The idle period 134 comprises of the device being in a low power deep sleep period (black regions) with occasional small duration wake-up cycles (white bands) to read sensor values. The current consumption during the wakeup periods in idle period 134 is also kept to a minimum with all high-powered components turned off.

Referring back to FIG. 2F, during deep sleep a small current load is present due to the cellular module 254 real time clock and SRAM flash memory, the GNSS block 272 hardware backup mode, and the IMU sensor, which are always on. The other sensors (i.e., the magnetometer and pressure sensor) are powered in an ultra-low power sleep mode. Additionally, all power is removed from the WiFi block 258 and other GNSS block 256 subsystems during deep sleep by keeping the load switches disabled.

Figure 9A:
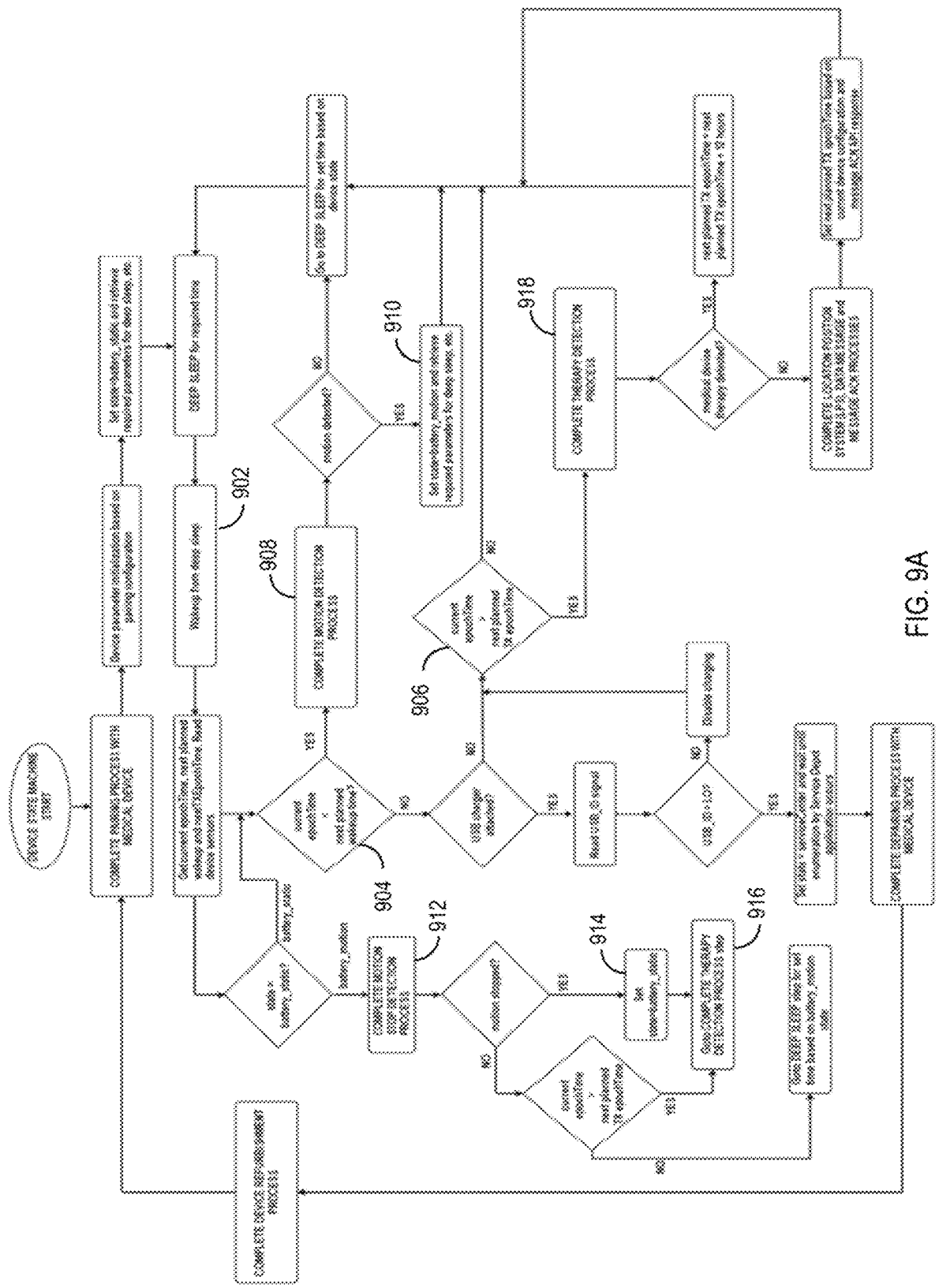
FIG. 9A is a diagram of the operational states for an asset tracker device, according to several embodiments.

Referring again to FIG. 1E, the LPS operation period 136 comprises the following operations: 1. GNSS receiver scan (FIG. 3A); 2. WiFi access point scan (FIG. 3A); 3. Cellular base station triangulation scan (FIG. 3B); 4. Location API endpoint call (FIGS. 5A-5B); 5. Message API endpoint call (FIG. 3D); 6. Wait one minute (FIG. 3D); or 7. Message Ack API endpoint call (FIG. 4B). The frequency and duration of the LPS operation period may depend on the state of the asset tracker device, for example, as shown in FIG. 9A.

Figure 3A:
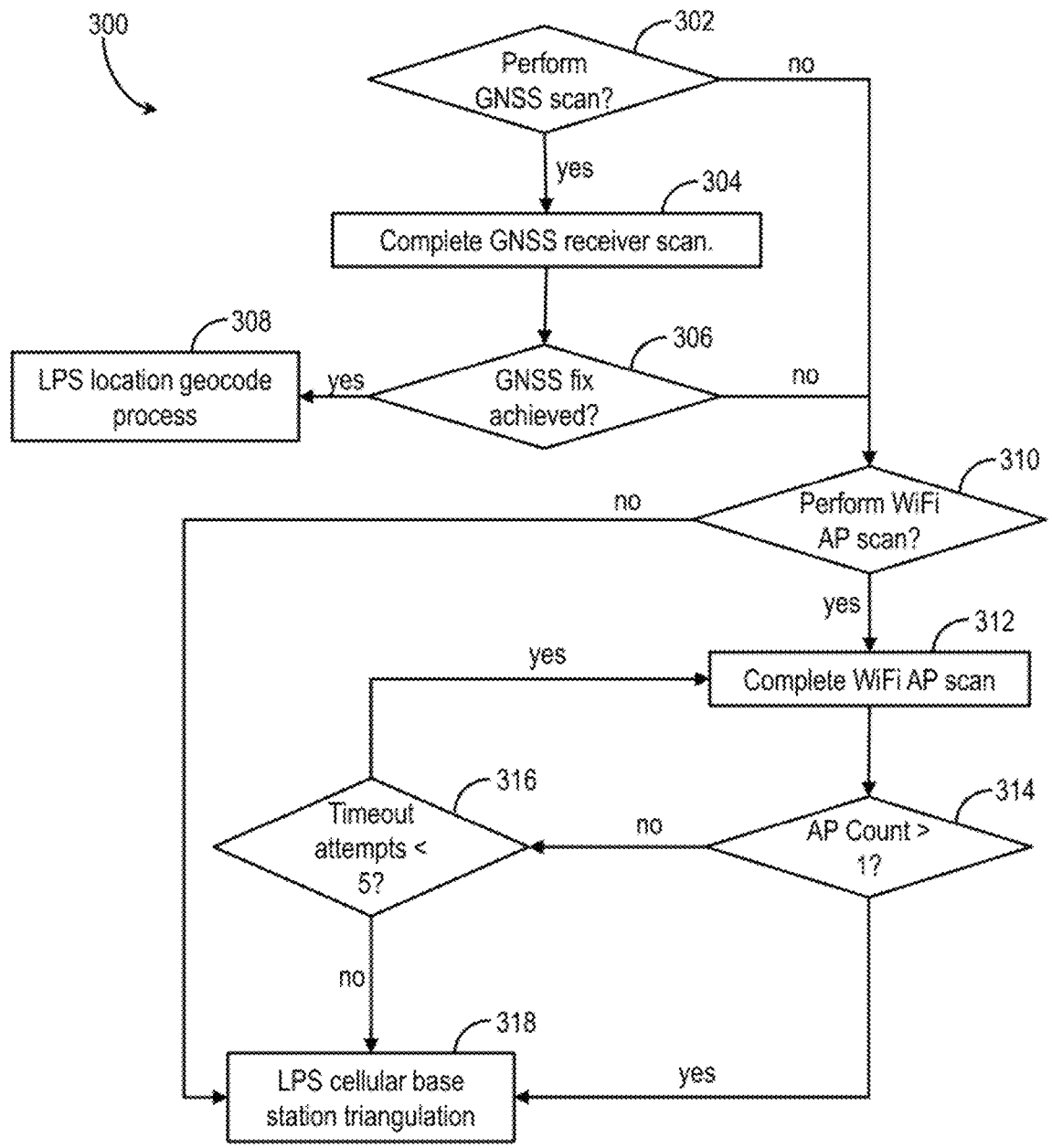
FIG. 3A is a flow chart of non-cellular LPS scans, according to an embodiment.

Now referring to FIG. 3A, illustrated therein is a flow chart of non-cellular LPS scans 300, according to an embodiment. Non-cellular scans include a GNSS receiver scan (304) and a WiFi access point scan (312). Non-cellular scans 300 are performed by an asset tracker device (i.e., asset tracker device 102 in FIG. 1A) during the LPS operation periods.

During performance of the non-cellular scans 300, the device queries whether to perform a GNSS receiver scan (302). If the response is affirmative, a GNSS scan is performed (304). For example, when the device is in motion or arrives to a new static location, a GNSS scan will be performed. If a GNSS location fix is not achieved (due to timeout) when the device is stationary and a WiFi AP scan (act 312) is successful, the next LPS scan will start with a WiFi AP scan first rather than a GNSS scan. If a GNSS location fix is achieved while the device is stationary, the next LPS scan will start with GNSS. The cloud system directs the device to perform as few operations as possible to minimize drain on the device battery as an optimization, i.e. perform the geolocation scan operation with the highest probability of success based on the recent past history of the device. If a GNSS fix is achieved (306), the non-cellular LPS operations 300 concludes and the LPS location geocode process begins (308).

If a GNSS scan is not performed, or a GNSS fix is not achieved, the device queries whether to perform a WiFi access point scan (310). If the response is affirmative, the WiFi access point scan is performed (312). If a device is in a location where GNSS geolocation fixes are achieved, then a WiFi scan is not performed. Since the GNSS receiver implements a hardware backup mode, subsequent scan attempts will typically succeed very quickly since the GNSS receiver will do a warm start.

It is advantageous to perform the GNSS scan (304) prior to the WiFi access point scan (312) since the comparative cost with respect to current and energy consumption is small for the GNSS receiver and is large for both the WiFi and the cellular radios. Additionally, the geolocation accuracy is high for the GNSS scan (304) compared to both the WiFi access point scan (312) and a cellular scan (FIG. 3B).

If more than one access point is not located at 314, the WiFi access point scan is performed up to five times (316). When more than one WiFi access point is located at 314, or if five attempts to located more than one access point fails, the non-cellular operations 300 conclude and an LPS cellular base station triangulation process begins (318).

Figure 3B:
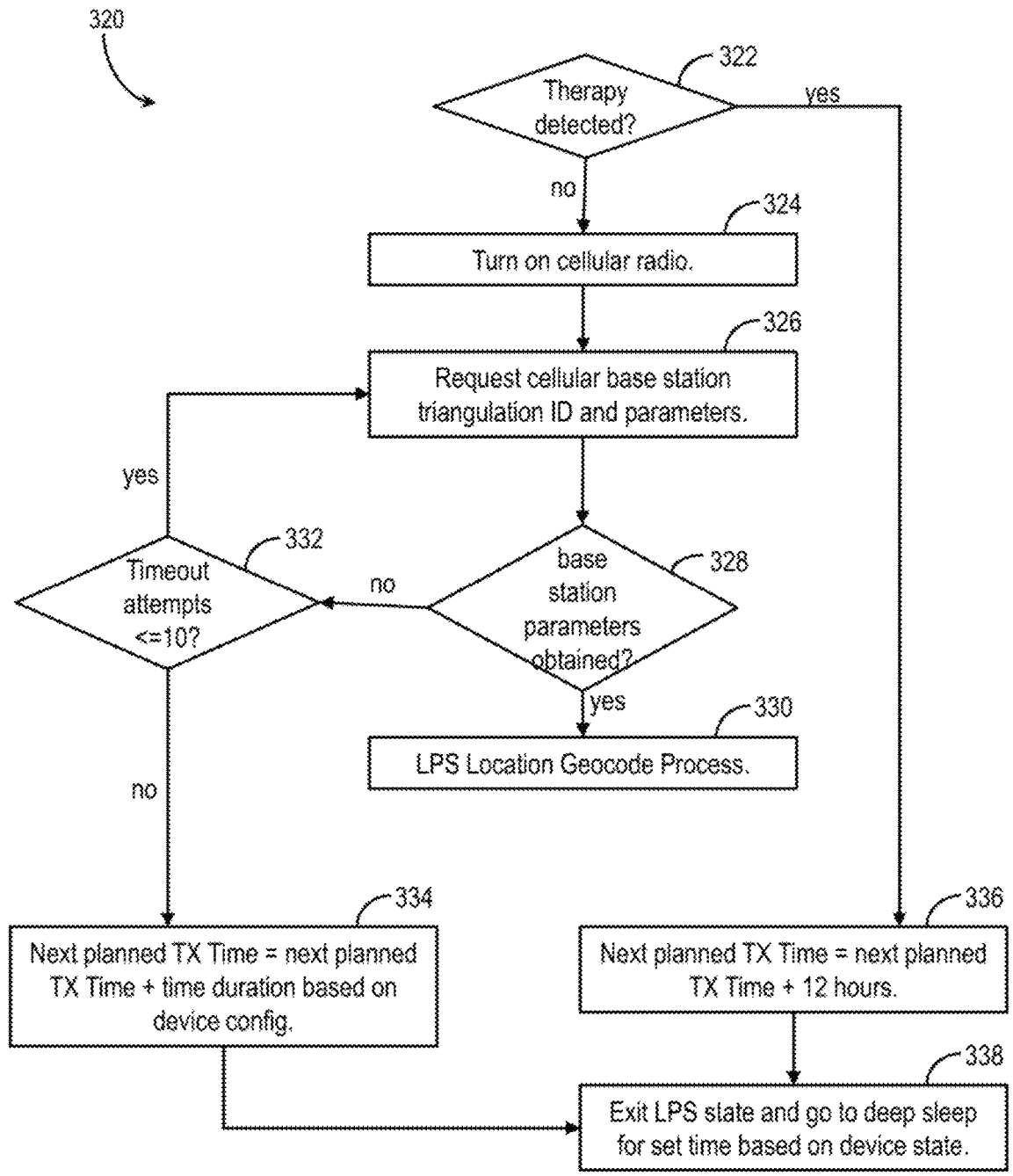
FIG. 3B is a flow chart of a cellular base station triangulation LPS scan, according to an embodiment.

Referring to FIG. 3B, illustrated therein is a flow chart of a cellular base station triangulation scan 320 LPS operation, according to an embodiment. The cellular scan 320 is performed by an asset tracker device (i.e., asset tracker 102 in FIG. 1A) during the LPS operation period.

At 322 the device queries whether a therapy is detected (i.e., whether the tracked medical device is in use), for example, by performing a scan as described below with reference to FIGS. 8A-9C. If a therapy is detected, the device calculates a next planned treatment time=next planned treatment time+12 hours (336). The device then exits LPS state and goes into deep sleep for a set time based on the device state (338).

If no therapy is detected at 322, the device's cellular radio is turned on (324). The device requests cellular base station ID and parameters from the connected and neighboring cellular base stations (326). If base station triangulation parameters are successfully obtained at 328, the cellular scan 320 is concluded and the LPS location geocode process begins (330).

The device attempts to request the cellular base station triangulation ID and parameters up to 10 times (322). If the parameters cannot be obtained, the device calculates a next planned treatment time=next planned treatment time+time duration based on device configuration. The device then exits LPS state and goes into deep sleep for a set time based on the device state (338).

To ensure that a geolocation fix can be attained in various usage environments from timber construction to steel and concrete, the asset tracker device implements an LPS system that can potentially geolocate using GNSS, WiFi access points or cellular base transceiver station triangulation. Once a geolocation fix has been obtained by GNSS scan, WiFi access point scan (FIG. 3A) or cellular base station triangulation scan (FIG. 3B), the LPS operation moves to a geocoding process to translate the fix information into address data.

Figure 3C:
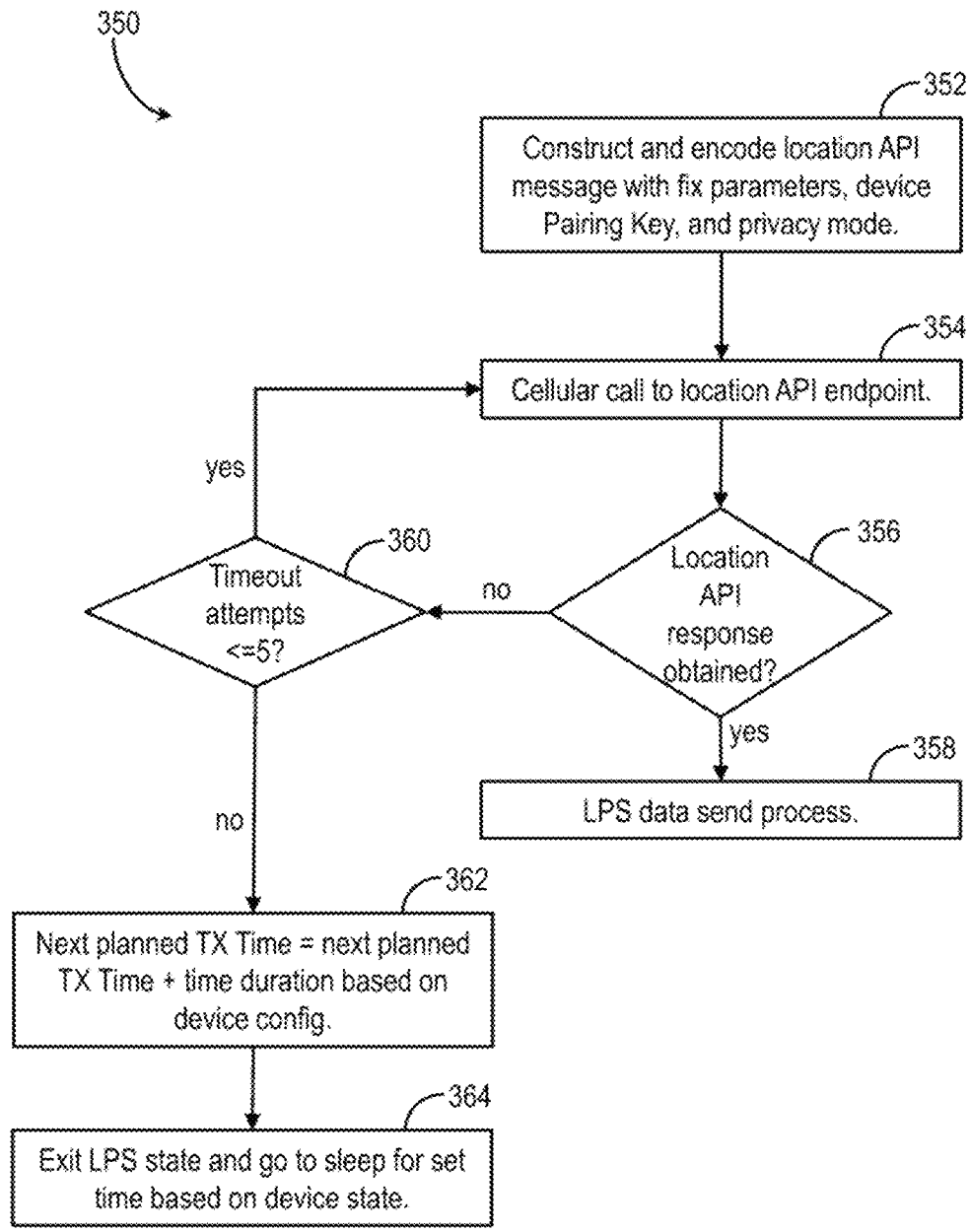
FIG. 3C is a flow chart of an LPS location geocoding process, according to an embodiment.

Referring to FIG. 3C, illustrated therein is a flow chart of an LPS location geocoding process 350, according to an embodiment. The geocoding process 350 is performed by an asset tracker device (i.e., asset tracker 102 in FIG. 1A).

At 352, the device constructs and encodes/encrypts a location API message. The message includes fix parameters including a device pairing key and privacy mode. The device makes a cellular call to the location API endpoint (354). If the location API endpoint responds at 356, the LPS data is sent to the device and the geocode process 350 is concluded (358).

If the location API response is not received after 5 attempts (360), device sets a next planned treatment time=next planned treatment time+time duration based on the device configuration (362), exits LPS state and goes into deep sleep for a set time based on the device state (364).

Following the geocoding process, LPS operation comprises messaging operations to transmit the geolocation data from the device into a message queue in the cloud system database via the message API endpoint and message acknowledge API endpoint.

Figure 3D:
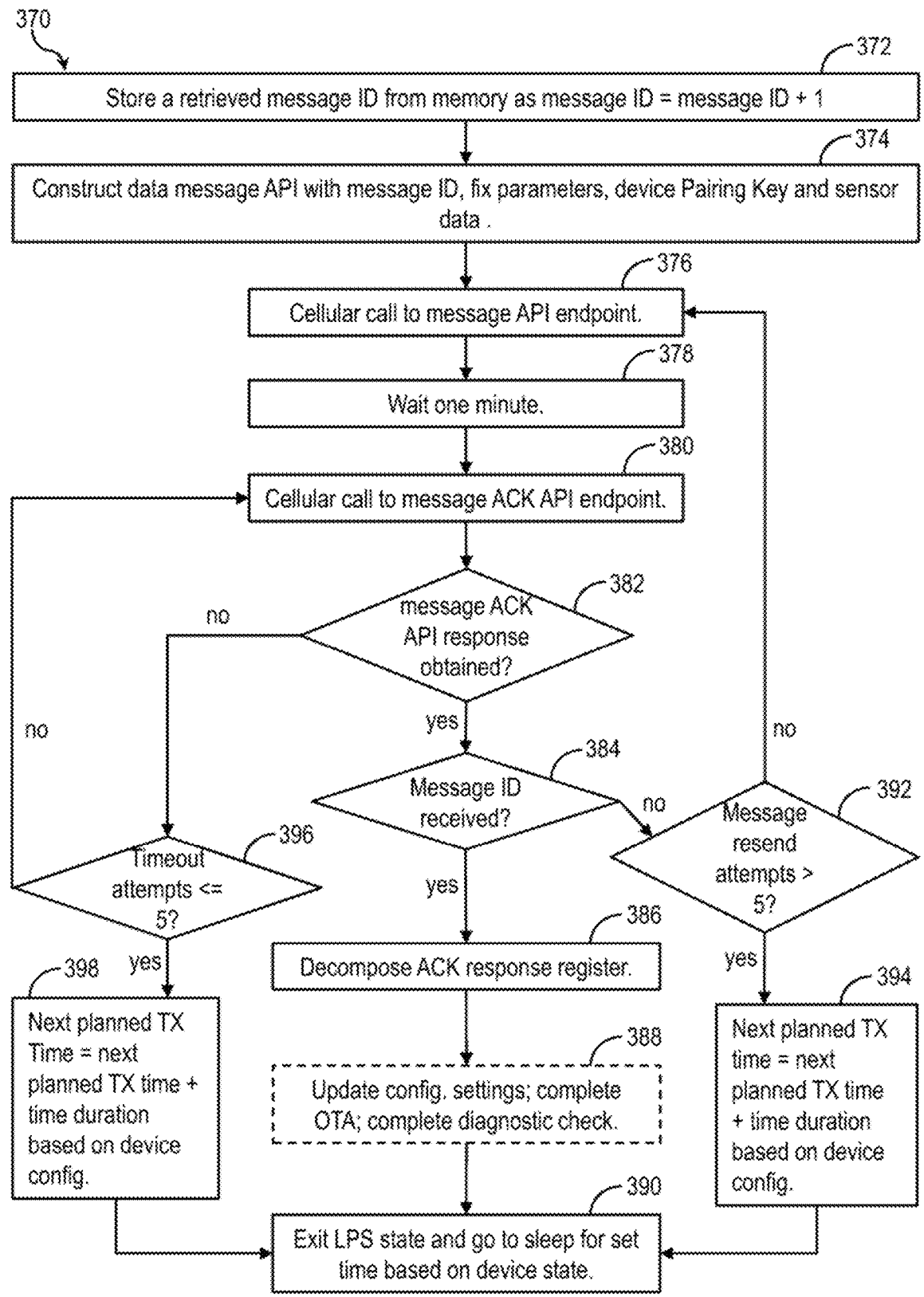
FIG. 3D is a flow chart of LPS messaging operations, according to an embodiment.

Referring to FIG. 3D, illustrated therein is a flow chart of LPS messaging operations 370, according to an embodiment. The LPS messaging operations are performed by an asset tracker device (i.e. asset tracker 102 in FIG. 1A).

The tracker device stores a retrieved message ID from its memory as message ID=message ID+1 (372). The device constructs a data message including the message ID, fix parameters, geolocation information, a device pairing key and sensor data (374). These parameters are communicated by the device to the message API endpoint for each operation cycle:

TABLE 1

Parameters included in data message.

| Parameter | Description |
| --- | --- |
| $t_{now_k}$ | Current time expressed in epoch time or UNIX time format. |
| $t_{next\_tx_k}$ | Next planned device data transmit time expressed in epoch time or UNIX time format. |
| $state_k$ | Current device state. |
| $T_{LPS_k}$ | Current LPS period. |
| $t_{gnss_k}$ | Duration of GNSS operations. |

TABLE 1-continued

Parameters included in data message.

| Parameter | Description |
|---|---|
| $t_{WF_k}$ | Duration of WiFi operations. |
| $t_{cell_k}$ | Duration of cellular operations. |
| $x_{SOC_k}$ | Battery State of Charge. |
| LPS fix type | Which method achieved the geolocation fix. |
| Sensor data | Various measurement data of device observations of external environment. |

Figure 4A:
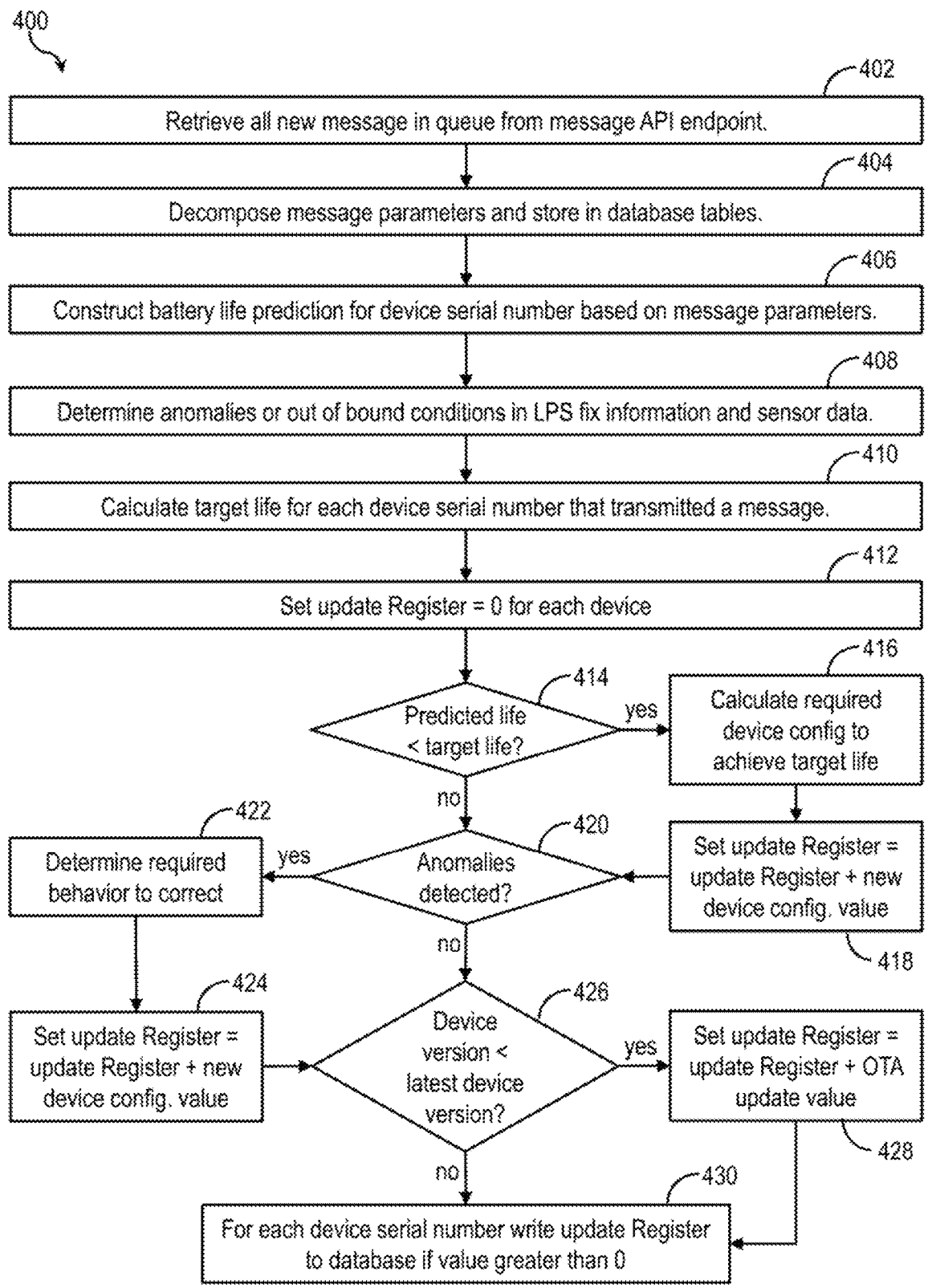
FIG. 4A is a flow chart of a cloud message processing CRON API process, according to an embodiment.
Figure 4B:
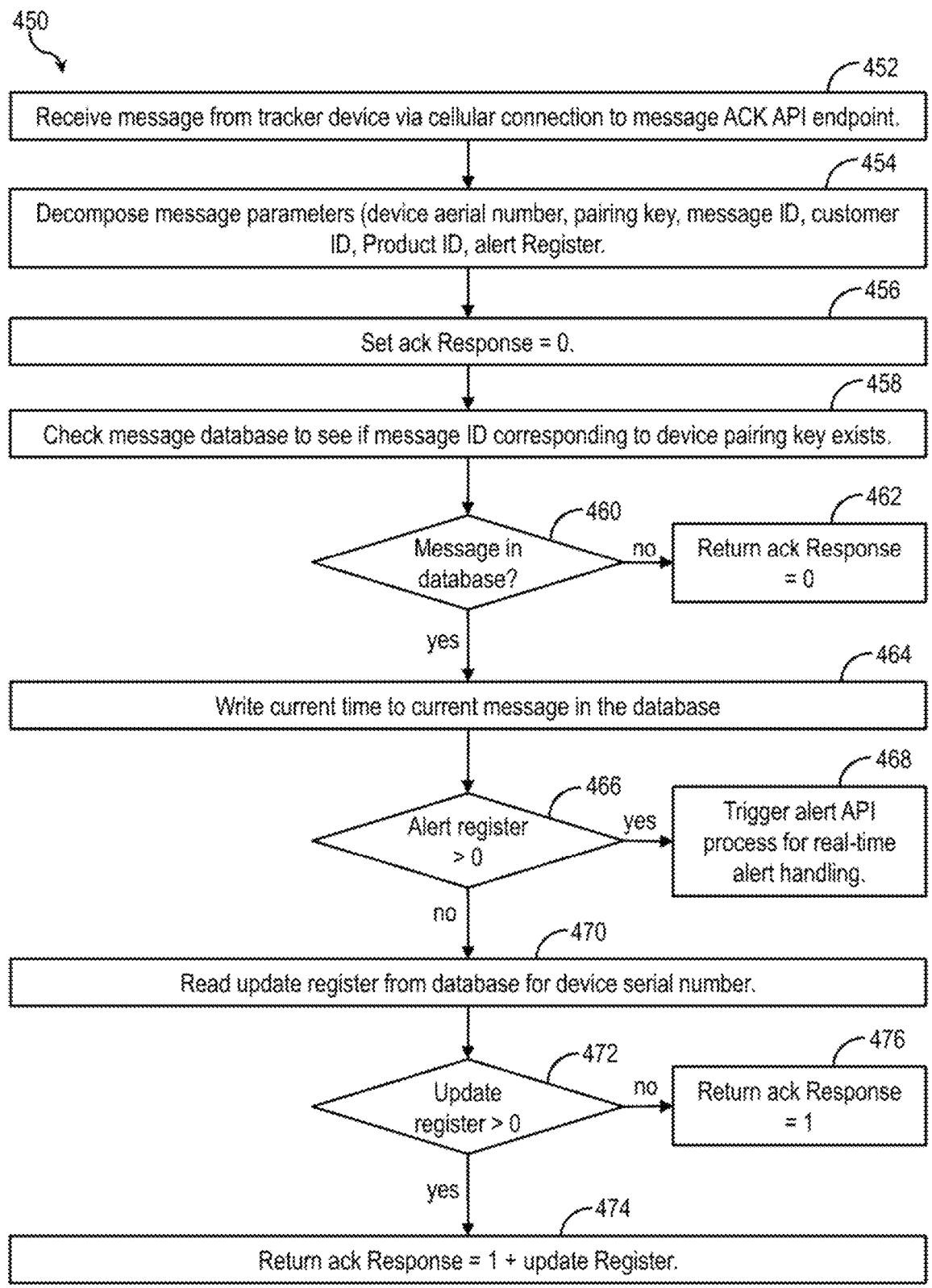
FIG. 4B is a flow chart of a cloud message acknowledge API endpoint process, according to an embodiment.

The device makes a cellular call to a message API endpoint to transmit the data massage to a backend cloud system (376). The device waits one minute (378) to allow the cloud system to process the message and provide feedback to the device (FIG. 4A). After a minute, the device calls a message acknowledge endpoint to verify the data message has been received and processed by the cloud system (380).

At 382, if an acknowledge response register is obtained from the message acknowledge endpoint, the device queries whether a message ID was received (384). If the message ID is received, the device decomposes the acknowledge response register (386). If required, the device updates its configuration settings, completes an OTA firmware update and completes a diagnostic check as required by the response register (388). The device then exits LPS state and goes into deep sleep for a set time based on the device state (390).

If the response register from the message acknowledge endpoint is not received after 5 attempts (396), or if the message ID is not received after 5 attempts (392), the device sets a next planned treatment time=next planned treatment time+time duration based on the device configuration (398, 394), then exits LPS state and goes into deep sleep for a set time based on the device state (390).

Figure 4C:
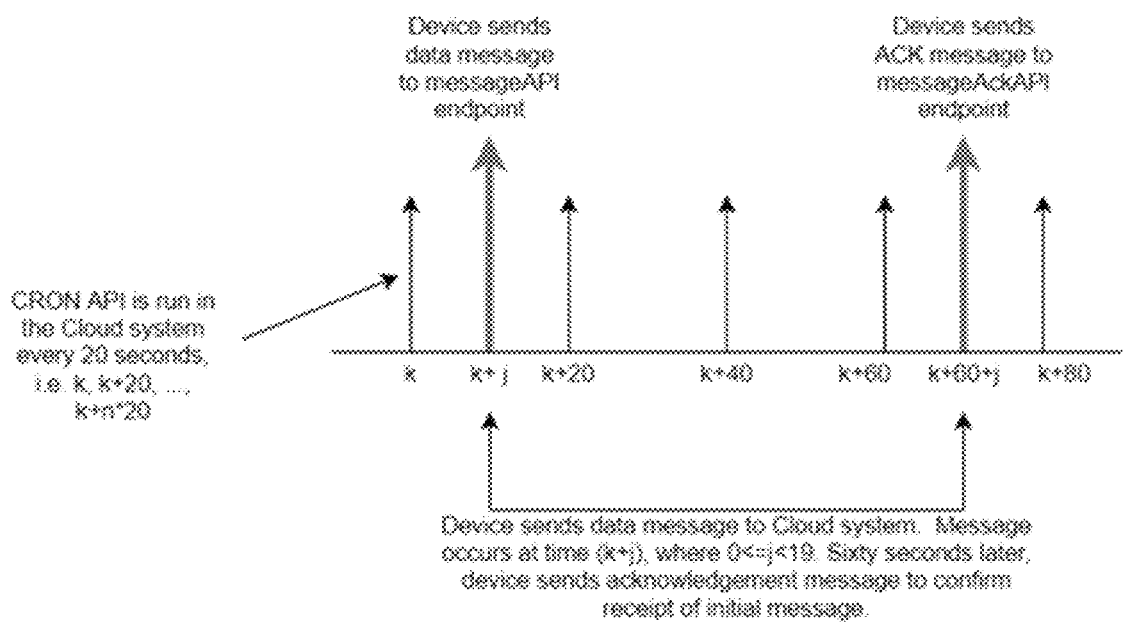
FIG. 4C is a diagram of the temporal execution of the CRON API process of FIG. 4A.

Now referring to FIG. 4A, illustrated there is a flow chart of a cloud message processing CRON API process 400, according to an embodiment. The message processing CRON API process 400 may be performed by message processing CRON API 110 in FIG. 1A. As shown in FIG. 4C, the CRON API process 400 independently runs every 20 seconds, scanning and processing new messages for ingestion. Once the message is sent to the message API endpoint, some time (<60 seconds) is required for the message to settle and be stored in the message queue table in the database. By running the CRON API every 20 seconds, this provides for sufficient time for the cloud system to process the message, perform analytics, pull in external inputs (anomalies, external inputs) and steer the device as a feedback control system (FIG. 1D).

Referring again to FIG. 4A, all new messages in a queue from a message API endpoint are retrieved (402). Each message is decomposed and message parameters (Table 1) are stored in requisite database tables (404).

A battery life prediction is constructed based on message input parameters shown in Table 1, above (406). In calculating the predicted battery life, the following parameters are assumed to be known based on knowledge of the asset tracker device physical implementation:

TABLE 2

Known parameters of the asset tracker device.

| Parameter | Description |
|---|---|
| $I_{deepsleep}$ | Deep sleep current of the device. |
| $t_{deepsleep_k}$ | Duration of deep sleep operation. |
| $I_{wakeup}$ | Wakeup current during idle mode. |

TABLE 2-continued

Known parameters of the asset tracker device.

| Parameter | Description |
|---|---|
| $t_{wakeup_k}$ | Duration of wakeup operations during idle mode. |
| $I_{selfdischarge}$ | Battery self-discharge current. |
| $I_{gnss}$ | GNSS receiver current during LPS mode. |
| $I_{WF}$ | WiFi radio current during LPS mode. |
| $I_{cell}$ | Cellular radio current during LPS mode. |

Based on the operation cycle model of FIG. 1D, the Coulombs consumed in each operation cycle during the idle period 134 and LPS operation period 136 can be defined as follows:

$$C_{idle_k} = (I_{deepsleep} \times td_{eepsleep_k}) + \qquad (3)$$
$$(I_{wakeup} \times t_{wakeup_k}) + (I_{selfdischarge} \times (t_{deepsleep_k} + t_{wakeup_k}))$$

$$C_{LPS_k} = (I_{gnss} \times t_{gnss_k}) + (I_{WF} \times t_{WF_k}) + \qquad (4)$$
$$(I_{cell} \times t_{cell_k}) + (I_{selfdischarge} \times (t_{gnss_k} + t_{WF_k} + t_{cell_k}))$$

$$C_{operation\_cycle_k} = C_{LPS_k} \times C_{idle_k} \qquad (5)$$

where $C_{idle_k}$ is the current consumption during the idle period 134, $C_{LPS_k}$ is the energy consumption during the LPS operation period 136. For reference, the other terms in equations (3), (4), and (5) are described in Table 1 and Table 2, above.

Thus, the current consumption values for each of the various operations, e.g. GNSS receiver, cellular radio, deep sleep, etc., are based on measurements and technical datasheet worst-case values, while the operation times within each operation cycle are variable. Additionally, the number of operation cycles for an asset tracker device is based on the LPS period, which can range anywhere from once every 10 minutes to once every 64 days.

With the above Coulomb consumption model, the following expression can be used to find the total number of device cycles based on total battery capacity assuming a fixed Coulomb consumption per operation cycle:

$$\text{Number device cycles} = \frac{\text{Total Coulombs in battery pack}}{C_{operation\_cycle_k}} \qquad (6)$$

For a fixed LPS period and Coulombs consumed during the LPS operation, we can determine the number of device cycles and translate the above expression into a battery life equation as follows:

$$\text{Battery Life (days)} = \text{Number device cycles} * \text{Period of device cycle} \qquad (7)$$

From here, mathematical expressions can be generated for remaining battery life based on variable LPS periods, variable Coulomb consumption in LPS operation, and current battery State of Charge. This allows the non-linear state space model (equations (1) and (2), above) to be rewritten as:

$$x_k = F(x_{k-1}) + \eta_k \qquad (8)$$

$$y_k = f(T_{LPS_k}) \times g(SOC_k) \times h(C_{LPS_k}) + v_k \qquad (9)$$

where $x_k$ is the system state vector at time step k defined as:

$$x_k = \begin{bmatrix} x_{T\_LPS_k} \\ x_{SOC_k} \\ x_{C\_LPS_k} \end{bmatrix} \qquad (10)$$

and where $x_{T\_LPS_k}$ is the LPS period of time step k, $x_{SOC_k}$ is the battery State of Charge (SOC) at time step k, $x_{C\_LPS_k}$ is the average Coulombs consumed during all prior LPS operations, and $y_k$ is the predicted battery life remaining value in days. For this implementation, a least squares linear regression model was used. According to other embodiments, alternate modeling approaches could be used such as Extended Kalman Filtering and artificial intelligence/machine learning methods.

Still referring to FIG. 4A, at 406, a battery life prediction is made for each unique device serial number that transmitted a data message since the prior CRON API cycle was executed.

Once the battery life prediction has been calculated, the target battery life is then compared to the predicted battery life $y_k$ as follows using the following cost function:

$$\forall_k = y_{k_{target}} - y_k \qquad (11)$$

Additionally, the LPS fix type of the most recent geolocation fix is reviewed against the last few prior LPS fix types for that device serial number. A reordering of the LPS scan will be done based on the device's prior LPS geolocation fixes. This approach is done to determine which LPS method should be used first to conserve the most battery life, as each operation is expensive from a Coulomb consumption and battery life perspective. The new LPS fix order will then be translated into a predicted LPS Coulomb consumption $C_{LPS_k}$ based on a priori information of the device LPS Coulomb consumption and the LPS fix order adjustments made.

At 412 an update register value for the device is set to 0.

If the predicted battery life is less than the target and the value of the cost function $\forall_k$ is high (414), the prediction model is recursively re-run using ever higher LPS periods $T_{LPS_k}$ and the new predicted LPS Coulomb consumption $C_{LPS_k}$, such that the error is less than a threshold value $\epsilon$ (416).

$$y_{k'} = f(T_{LPS_{k'}}) \times g(SOC_k) \times h(C_{LPS_{k'}}) + v_k \qquad (12)$$

$$\forall_{k'} = y_{k_{target}} - y_{k'} \leq \epsilon \qquad (13)$$

If the recursive calculations find that the cost function $\forall_{k'}$ cannot be minimized below the threshold value E, then parameters are chosen such that the cost function $\forall_{k'}$ is at a minimum. This case would be considered a non-optimal prediction and an alert in the cloud-based system could be generated to allow for possible proactive measures if required.

This procedure then determines the new LPS period $T_{LPS_k}$ and LPS fix type of the device. Both the new LPS period $T_{LPS_k}$ and preferred LPS operation order are combined into an update Register and stored into the device database (418).

Additionally, data anomalies for each asset tracker device are reviewed on a higher period through separate independent running CRON API processes (420). These CRON API processes can use various forms of analytics regression, anomaly detection, specific business rules based on customer, etc. with the results being stored into a cloud database.

Furthermore, external condition changes to the asset, which may be unknown to the device, and input into the Cloud-based database can precipitate a change in device behavior. For example, a medical device may experience one of the following significant events: preventative maintenance of the medical device is overdue; a field corrective action (FCA) recall on the medical device is issued by one of the governing health bodies, e.g. FDA, Health Canada; or a patient death has occurred while using the medical device.

In each of the above examples, it may be critically important to locate the medical device and the asset tracking device's frequency of transmission can be increased accordingly. These behavior changes can be implemented through an http or web interface that allows a user to input data informing the cloud system of the critical event (422). The critical event data input from the http or web interface will trigger an API process that will store the required behavior change into the cloud database (424).

In determining the required behavior at 422, the types of possible feedback to the device from the cloud system include the following non-exhaustive list of behaviors: thresholds for motion detection and absence of motion, whereby the CRON API compares last five locations with last five device states (for example if device is in a motion state, yet location is unchanged, increase the motion thresholds, and conversely, if device is in a static state, yet location is changed, decrease the motion thresholds); significant drop impact, which can be measured through the accelerometer or IMU of the asset tracking device; diagnostic check of certain subsystem based on anomaly detection; OTA firmware update required to address defects (426, 428); turn off certain subsystem due to observed defect(s) or anomalies; shutdown due to possible tamper events; adjust frequency of transmission due to extreme temperatures observed by the device; adjust behavior of device due to specific geolocation, time of year, etc.; and adjust behaviour of device due to condition changes for the tracker device.

These changes in behavior or actions are then encoded and stored into a behavior update register (430). CRON API function process then reads this register and combines this with the update Register as follows:

$$\text{update Register} = f(\text{battery life prediction}) \qquad (14)$$

$$\text{behaviour Update} = \qquad (15)$$
$$f(\text{anomaly detection}) + f(\text{external condition changes})$$

$$\text{update Register} = \text{update Register} + \text{behaviour Update} \qquad (16)$$

Following execution of the cloud message processing CRON API execution 400, the device will then confirm receipt of the current message by the Cloud system using a message acknowledge API endpoint which returns an acknowledge response, as shown in FIG. 4B.

Now referring to FIG. 4B, illustrated therein is a flow chart of a cloud message acknowledge API endpoint process 450, according to an embodiment. The ACK API endpoint process 450 may be performed by message ACK API endpoint 112 in FIG. 1A.

The acknowledge API endpoint execution 450 is initiated when the tracker device sends a data message to the message acknowledge API endpoint (452). The message is decomposed to message parameters including a device serial number, a pairing key, a message ID, a customer ID, a product ID and an alert register value (454). At 456, an acknowledge response value is set to 0.

The cloud database is searched to determine if the message ID corresponding to the pairing key exists (458). If a message does not exist in the database, the acknowledge response value=0 is returned to the device acknowledge response register (462), wherein the acknowledge response register has the following definition:

$ackResponse =$
$\begin{cases} 0 \text{ (message not received, resend required)} \\ 1 \text{ (message received and no additional action required)} \\ 1 + updateRegister \text{ (message received and additional action required)} \end{cases}$ If, at 460, a message is found in the database, the current time is written to the current message, received at Act 452, in the database (464).

If, at 466, the alert register value of the message is greater than 0 then an alert API process for real-time alert handling is spawned and triggered by the ACK API endpoint by sending an internal message into a trigger queue (468). The alert API process is not a CRON process, i.e. scheduled at a fixed time/frequency. The alert API process is triggered through an internal message queue trigger within the cloud system. If the alert register value is not greater than 0, the update register for the device's serial number is read (470).

If the update register value is not greater than 0, the acknowledgement response value=1, is returned to the device acknowledge response register (476). If the update register value is greater than 0, then the acknowledgement response value=(1+update register value) is returned to the device (474).

Following act 474, the tracker device will then decompose the acknowledge response register and adjust the configuration and behavior of the device based on the instructions received from the cloud system and the device operational state (FIG. 9A). This implementation approach allows for adaptive control based on machine learning/artificial intelligence methods of back end system with feedback steering each device uniquely to an optimal output. The optimal output may be, for example, scaling of transmission frequency to extend battery life; optimized LPS operations based on current environment; adjustable device thresholds due to regression analysis; or anomaly detection in the database.

According to an embodiment, cloud message acknowledge API endpoint execution 450, may be implemented for real-time tracking of temperature with modifications to the asset tracker device and the cloud system. Temperature tracking could be achieved, for example, by addition of an external temperature probe and associated circuitry on the tracker device and configuring the tracker device to sample and store external temperature data over time. Similarly, the message API endpoint may be configured to support parsing of data messages from temperature tracker devices and storing the same in the database. Similarly, the adaptive feedback control system shown in FIG. 1D may be modified to support temperature tracking by, for example, increasing device communication frequency with the cloud system (e.g. every 10 to 15 minutes) during transportation and decrease communication frequency (e.g. every 2 hours) once the shipment has arrived at the programmed destination. Arrival at the destination may be determined using the Haversine formula, to calculate distance between a device location and a destination and compare against a threshold:

$$\text{distance\_between}_{device, destination} \le \epsilon \quad (17)$$

Figure 5A:
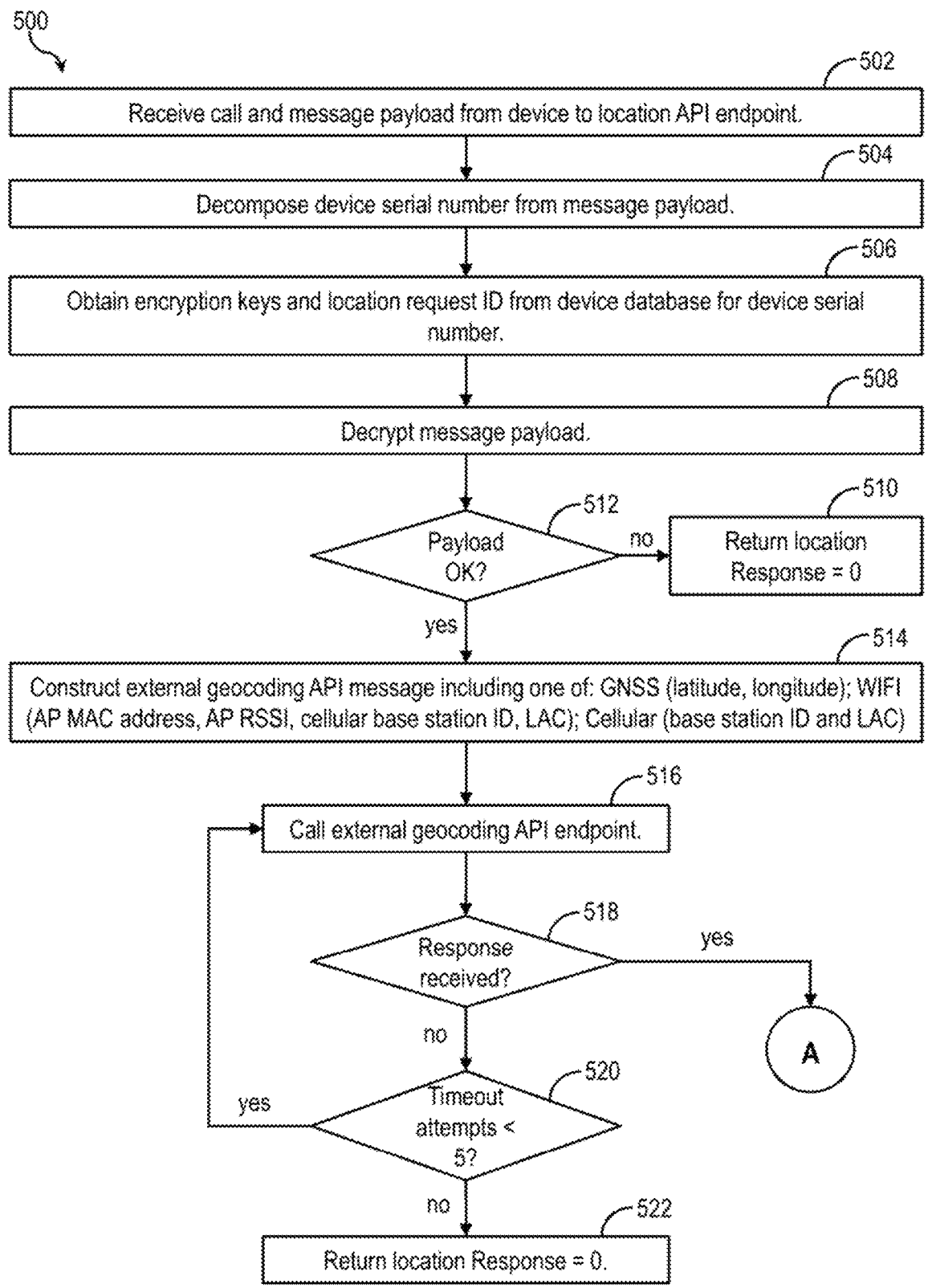
FIG. 5A-5B is a flow chart of a location API endpoint call operation, according to an embodiment
Figure 5B:
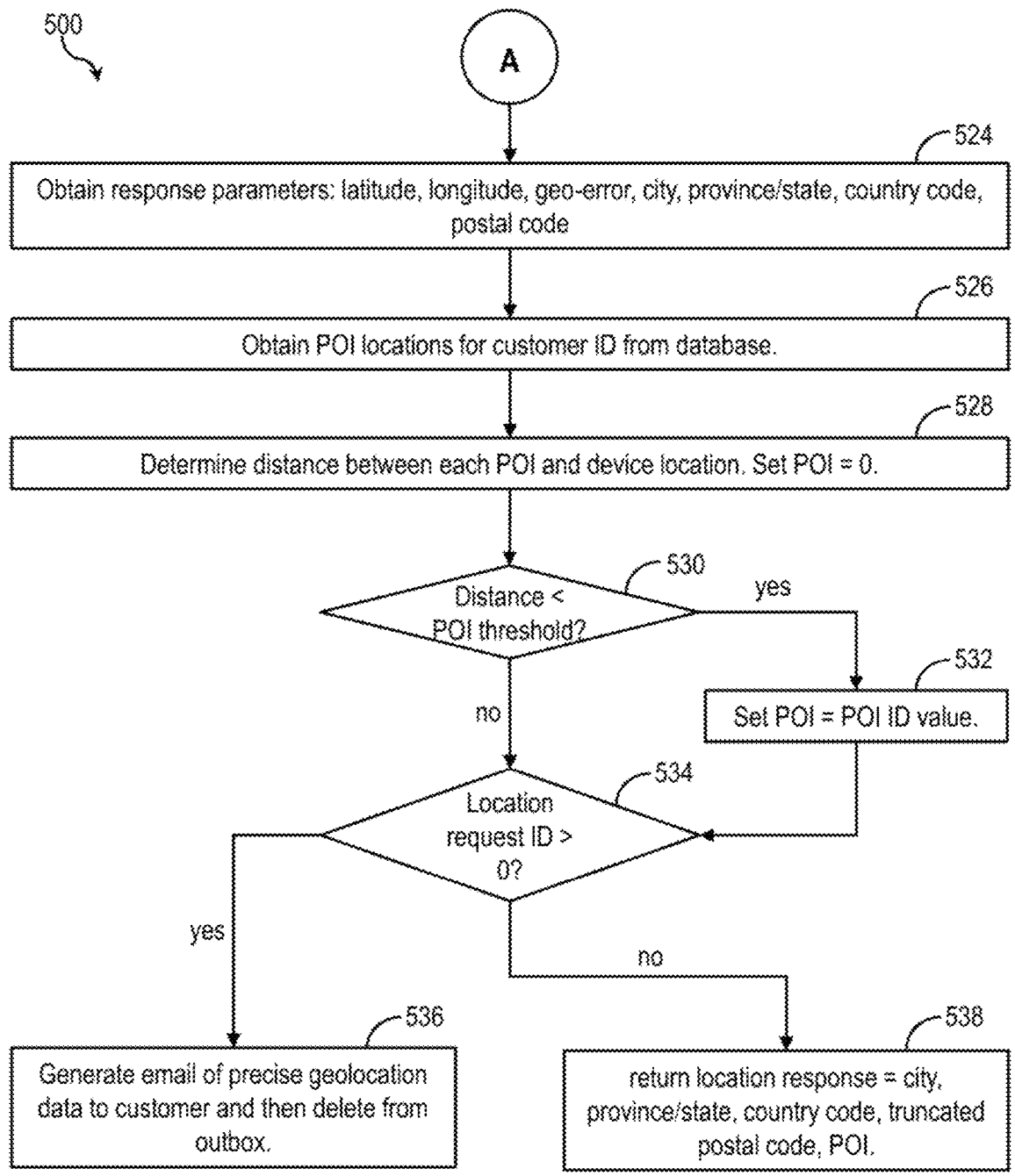

Referring to FIGS. 5A-5B, illustrated therein is a flow chart of a location API endpoint call 500 LPS operation, according to an embodiment. The location API endpoint call may be performed by the location API service 152 in FIG. 1B.

A call and the message payload from an asset tracker device are received at the location API endpoint (502).

The message payload is decomposed to message parameters including a device serial number (504). Generally, the device serial number is not encrypted in the payload, as this information is required to obtain the encryption keys from the database. According to an embodiment, the device serial number may be encrypted using, for example, a universal encryption key.

The cloud database is searched to obtain a location request ID and encryption keys for the device serial number (506). Once the device serial number is decoded from the locationAPI message payload, the encryption keys for that device are requested from the Cloud-based database and the remainder of the payload message is decrypted (508). For added security and privacy, the geolocation data obtained is never stored and collected (i.e. at rest) and is always maintained secure and encrypted in transit for the duration of method 500.

At 512, the decrypted payload is confirmed to have the contents in Table 3, according to the LPS fix type for the message payload.

TABLE 3

| LPS Fix Payload Contents. | |
|---|---|
| LPS Fix type | Payload contents |
| GNSS | Latitude, longitude, geo-error. |
| WiFi | MAC access point (AP) addresses and RSSI value for each AP; cellular serving base station ID (CID), location area code (LAC) and RSSI value. |
| Cellular Serving Cell and Neighbor Cells | Cellular base station ID (CID), location area code (LAC) and RSSI values. |

In constructing the geocode message payload, the payload contents in Table 3 could be considered as personally identifiable information. This information must be securely translated into an anonymized location to ensure the privacy of patients. Therefore, the message contents are encrypted by the device using encryption keys that are known only by the device and the back-end cloud database (504-508). There are many different possible encryption methods and options that can be used and one skilled in the art can reasonably develop a suitable method, which is outside the scope of this invention.

If, at 512, the payload is not correct, a location response value=0 is returned to the tracker device and the method 500 concludes (510). For example, there may be circumstances of data corruption due to device errors, transmission errors, or possibly due to potential counterfeit that may result in an incorrect payload. Thus, if such a situation arises, the method 500 provides reliability and resiliency against unforeseen circumstances.

If the payload is correct at 512, a message is constructed for an external geolocation and geocoding API (514). There are numerous commercially available solutions that keep the data only in transit and never store the information, i.e. at rest. Additionally, by abstracting the call to the external geolocation and geocoding API endpoint service from the location API endpoint, there does not exist any connection of the location request to the original asset tracking device.

The external geocoding API endpoint is called (516). If no response is received in five attempts (520), a return location response value is set to 0 (522).

If, at 520, a response is received from the external geocoding API endpoint, the location API obtains response parameters, including: latitude, longitude, geo-error, city, state/province, country code and ZIP/postal code (524).

Points of Interest (POI) including latitude, longitude and a POI ID are retrieved for the customer ID from the cloud database (526). By maintaining the list of POIs within the device databases, this allows for a reduction of CPU operations by the device. This approach also reduces code complexity since the POI locations do not need to be hardcoded into the device firmware. Additionally, the POI list can be easily modified by simply adjusting entries in a database without modifications to any software code.

A distance between each POI and the tracker device is calculated for each POI; the POI value is set=0 (528). The Haversine formula is run against each Point of Interest location to determine distance of the device to the POI. The Haversine formula is described below and the distance $d_k$ in meters is calculated for each POI location as follows:

$$a = \sin^2\left(\frac{lon_d - lon_{POI_k}}{2}\right) + \cos(lat_d) \times \cos(lat_{POI_k}) \times \sin^2\left(\frac{lon_d - lon_{POI_k}}{2}\right) \quad (18)$$

$$c = 2 \times \text{atan2}(\sqrt{a}, \sqrt{1-a}) \quad (19)$$

$$d_k = 6372795 \times c \quad (20)$$

where $lat_d$ and $lon_d$ are the latitude and longitude of the asset tracker device returned from the external geolocation and geocoding endpoint API. And where $lat_{POI_k}$ and $lon_{POI_k}$ are the latitude and longitude coordinates for the kth customer POI location.

If, at 530, the distance $d_k$ is found to be less than a threshold, (e.g. 100 m for GNSS fix type), then the device is assumed to be located at this Point of Interest location and the POI value is set=POI ID value (532). If the distance $d_k$ is greater than the required thresholds, then the POI value remains at =0 to indicate that the device is not located at a Point of Interest.

If, at 534, the location request ID (acquired at Act 506) is not greater than 0, the location API endpoint returns to the device the following an approximate geolocation, which has been stripped of all possible PII information (538). The approximate geolocation area is provided as: a city; a state/province; a country; a POI location; or a truncated ZIP or postal code. For example, postal codes are normally comprised of district and sector, with the sector being precise. Thus, a postal code may be truncated to include only the wider district identifier.

An advantage of the method 500 is that an owner of the medical device can define a set of Points of Interest that reflect non-patient locations such as service depots, logistic warehouses, hospitals and clinics. By including the POI check (528) in the location API endpoint call 500, a precise location information in the form of the POI ID can be provided back to the device when the asset tracker and medical device pair are located in one of these non-patient specific related locations. A further benefit, is that customers may manage their inventory levels, while maintaining patient privacy.

An additional feature that can be implemented, is a geolocation request for cases when devices have gone lost, missing, or stolen. In these instances, the medical device owner must provide a waiver and signoff to allow for specific geolocation information to be provided. Once provided, the location request ID is generated and stored in the database along with device serial number and customer email contact information.

In such case, at 534, the location request ID is greater than 0, and an email can be generated, sent with the precise geolocation information, and then deleted off the email server (536). This additional process allows for no PII information to ever be maintained in the device database yet allowing for the customer to precisely locate lost or missing medical devices. The customer may locate lost/missing medical devices, for example, by accessing the anonymized geolocation information via a web portal interface to the cloud system and by making a request for the precise geolocation information.

Thus, the location API endpoint call operation 500 ensures that all the information handled by the location API endpoint is always in transit and encrypted. No data is ever stored at rest. Therefore, this distributed asset tracking method achieves the ability to generate geolocation information that is anonymized with respect to the patient, and keeps all information including PII elements encrypted in transit throughout the entire process.

Figure 6A:
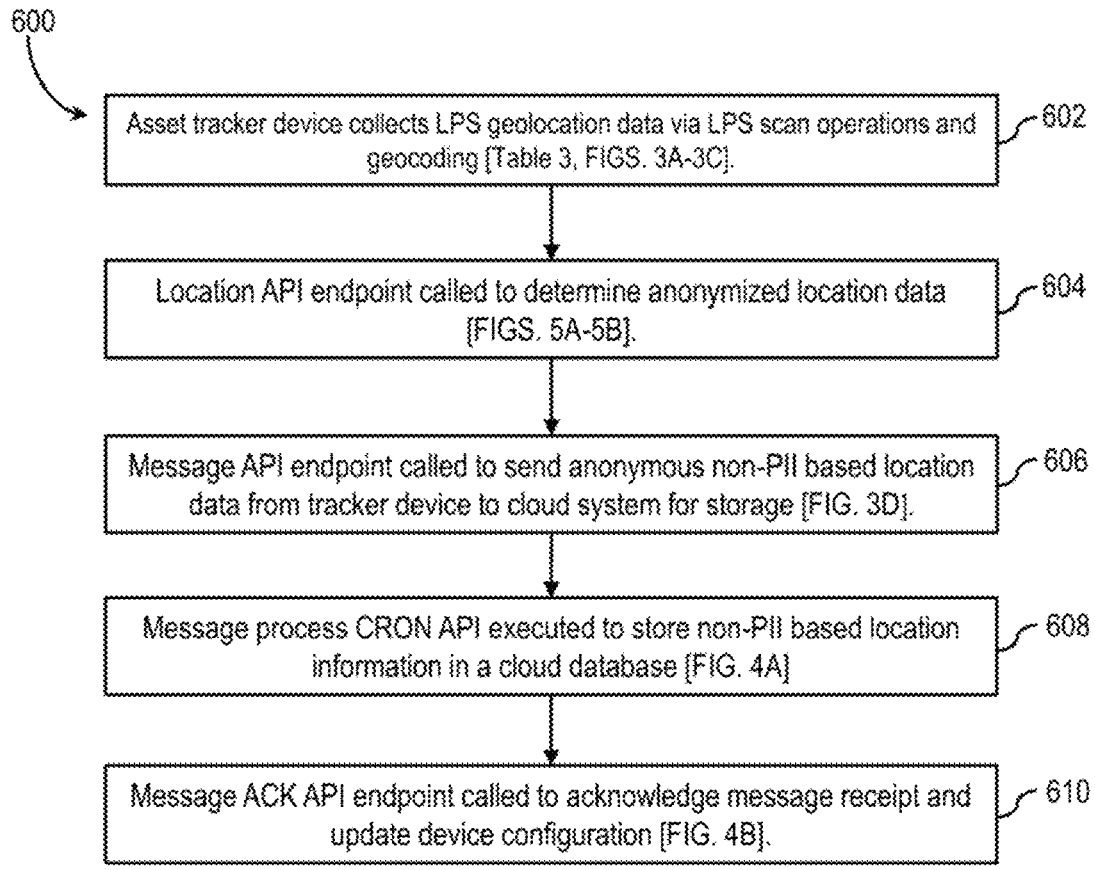
FIG. 6A is a flow chart of a privacy framework for anonymized geolocation and asset tracking, according to an embodiment.

While FIGS. 3A-5B illustrate various processes separately, the same processes may be jointly implemented in a privacy framework. Now referring to FIG. 6A, illustrated therein is a flow chart of a privacy framework for anonymized geolocation and asset tracking 600, according to an embodiment. The privacy framework 600 may be implemented using the systems 100 and 150 in FIGS. 1A and 1B, respectively.

At 602, an asset tracker device collects geolocation data (Table 3) via LPS scan operations (FIGS. 3A-3B) and geocoding operations (FIG. 3C).

At 604, the tracker device calls the location API endpoint of a cloud system to acquire anonymized location data (FIGS. 5A-5B).

At 606, the tracker device calls the message API endpoint to send anonymous non-PII based location data to a cloud system for storage (FIG. 3D).

At 608 the message CRON API is executed to store non-PII based location data in a cloud database (FIG. 4A). Act 608 is performed while the tracker device is waiting for one minute (FIG. 3D at 378) during an LPS operation period.

At 610, the tracker device calls the message acknowledge API endpoint to acknowledge message receipt and receive an update register value to modify the device configuration/behavior.

The privacy framework 600 provides a robust and secure asset tracking system and method that may be modified for specific tracking tasks, for example, tracking an asset's elevation above ground level. Elevation tracking may be desirable to estimate the approximate floor level of a medical device within a hospital or high-rise.

Figure 6B:
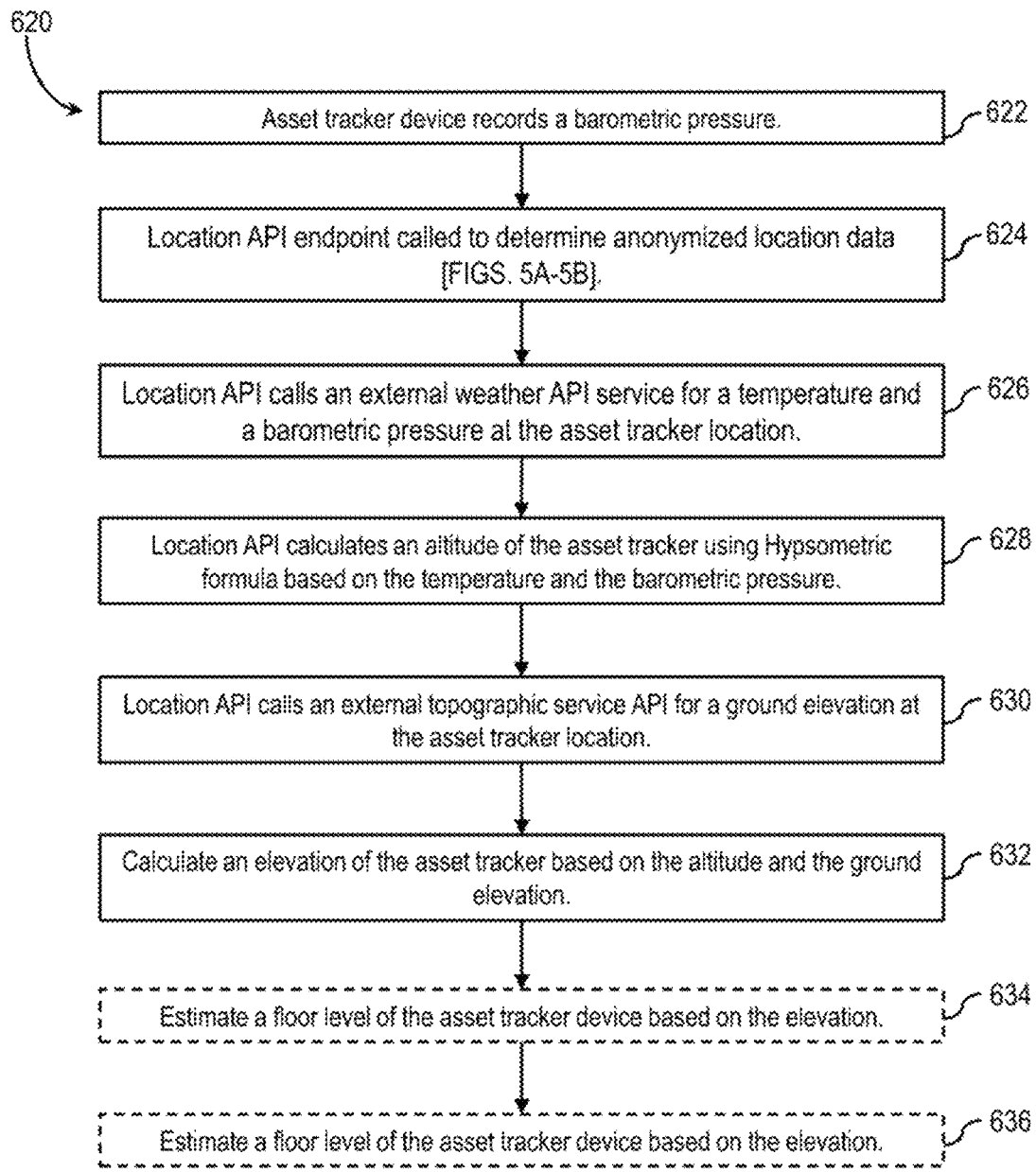
FIG. 6B is a flow chart of a method for elevation tracking of an asset, according to an embodiment.

Referring to FIG. 6B, illustrated therein is a method 620 for elevation tracking of an asset 620, according to an embodiment. The method 620 may be implemented using the systems 100 and 150 in FIGS. 1A and 1B, respectively, with modifications as described below.

At 622, an asset tracker device records a barometric pressure reading. The asset tracker includes a pressure sensor, and is configured to: record a barometric pressure reading; include the pressure reading in a location API endpoint call; include parsing and data storage for an elevation above ground level value in location API endpoint response and include the elevation above ground level value in a message API endpoint call.

At 624, the tracker device calls a location API endpoint to determine anonymized location data (latitude, longitude) of the tracker device as shown in FIGS. 5A-5B at 502-524. The message payload received from the tracker device further includes the barometric pressure reading.

At 626, the location API calls an external weather API service. The external weather API service will return a current external temperature and a sea level barometric pressure at the asset tracker current location based on the raw geolocation data (latitude, longitude) determined at 624. It is noted that the external temperature cannot be reliably read by the asset tracker device, as it could be located indoors in a climate-controlled environment. According to an embodiment, the weather API service may return a value for external weather conditions.

At 628, the location API is configured to calculate the altitude at the asset tracker device current location using the Hypsometric formula:

$$\text{altitude} = \left( \frac{\left(\left(\frac{P_o}{P}\right)^{\frac{1}{5257}} - 1\right) \times (T + 273.15)}{0.0065} \right) \quad (21)$$

Where: Po is sea level pressure returned by the external weather service API, P is the atmospheric pressure at the current location measured by the tracker device, and T is the current temperature at the current location returned by the weather service API. It is noted that formula 21 is only valid for altitudes below 11 km, which will cover most possible use cases.

At 630, the location API is configured to call an external topographic service API. In the United States, the US Geographic Service has a detailed topographic database that stores ground elevation across the United States. In Canada, the National Research Council has a comparable database and service. The topographic service API will return a ground elevation for the asset tracker current location based on the raw geolocation data (latitude, longitude) determined at 624.

At 632, the location API is configured to calculate an elevation above ground level for the tracker device as follows:

$$\text{elevation above ground level} = \text{altitude} - \text{ground elevation} \quad (22)$$

At 634, a building floor level estimate may be calculated by assuming a typical height per floor level.

At 636, the location API may be configured to return the elevation above ground level calculated at 632 and/or the ground floor estimate calculated at 634, so long as this information includes only non-PII location information. Where 636 is performed, the message API is further configured to parse and store the elevation above ground level. It is noted that Act 636 is generally only performed in cases where a location request ID (FIG. 5B at 534) exists for the current asset tracker device, e.g. lost, missing, or stolen devices.

An advantage to method 620 is that it leverages data already collected by the asset tracker and has minimal impact on device operations and power consumption/battery life, as virtually all operations have been shifted to the Cloud-based system (FIG. 1B). Another further advantage is that the method 620 provides more accurate altitude calculation than relying solely on GPS/GNSS systems which, have a higher level of altitude error due to factors such atmospheric effects and geoid height.

The method 620 may also be leveraged for temperature tracking applications according to embodiments wherein the tracker device includes a temperature sensor and an external weather condition is returned at 626. In temperature-controlled shipments, such as in the pharmaceutical industry, the controlled goods can be packed in cardboard boxes with insulative material and cooling gel packs. In these circumstances, external weather conditions will present a thermal load to the shipment. In cases where the controlled good temperature goes outside of its limits, knowledge of the external conditions may be useful in determining the cause of the issue and creating mitigations to avoid in the future.

Referring back to FIG. 6A, the privacy framework 600 provides a robust and secure asset tracking system and method that may be modified for specific anonymized tracking tasks, for example, the tracking of assets that are in transit by airplane. Regulations in most jurisdictions prohibit use of cellular devices during flights, particularly at take-off and landing. Traditional means have been devised to restrict cellular operation by measuring changes in acceleration or velocity during takeoff, or by measuring changes in the barometric pressure.

However, there are limitations to the traditional approaches. GNSS scanning for determining acceleration or velocity is hindered by the metallic aircraft body; measuring the changes in acceleration and/or velocity requires a relatively long sampling times and is computationally intensive, adversely affecting battery life of a tracker device; measuring changes in pressure may be hindered by a pressurized vs. non-pressurized aircraft cabin (depending on the aircraft used); and pressure changes may be exaggerated or difficult to detect when taking-off or landing at higher vs. lower altitude airports.

According to an embodiment, the privacy framework 600 can be modified to provide an asset tracking system and method that complies with restrictions on cellular device use during flights to allow for the asset tracker device to only allow cellular transmission when on the ground. The modifications to framework 600 would be:
  1. Configure the tracker device to ensure a motion-based communication period is sufficiently small to capture time between arrival at airport and airplane takeoff.
  2. Add list of all airport geolocations to POI list in cloud database for use in Haversine distance calculation. The airport location subset range in POI list should be well defined and unique.

3. During the data message and acknowledgement process, the cloud system is updated to recognize airport proximity and set the update register and acknowledge response register values accordingly to a unique action based on airport proximity.
4. Asset Tracker device behavior is modified based on acknowledge response to restrict cellular operation for 24 hours to ensure no cellular transmission during flight and consider reducing frequency of other operations to conserve power by eliminating need for airplane take-off detection algorithms.

The advantage of this approach is that impact to battery life of the tracker device and the complexity of the tracker device operations is minimized by eliminating the need to develop robust airplane takeoff detection algorithms.

Figure 7A:
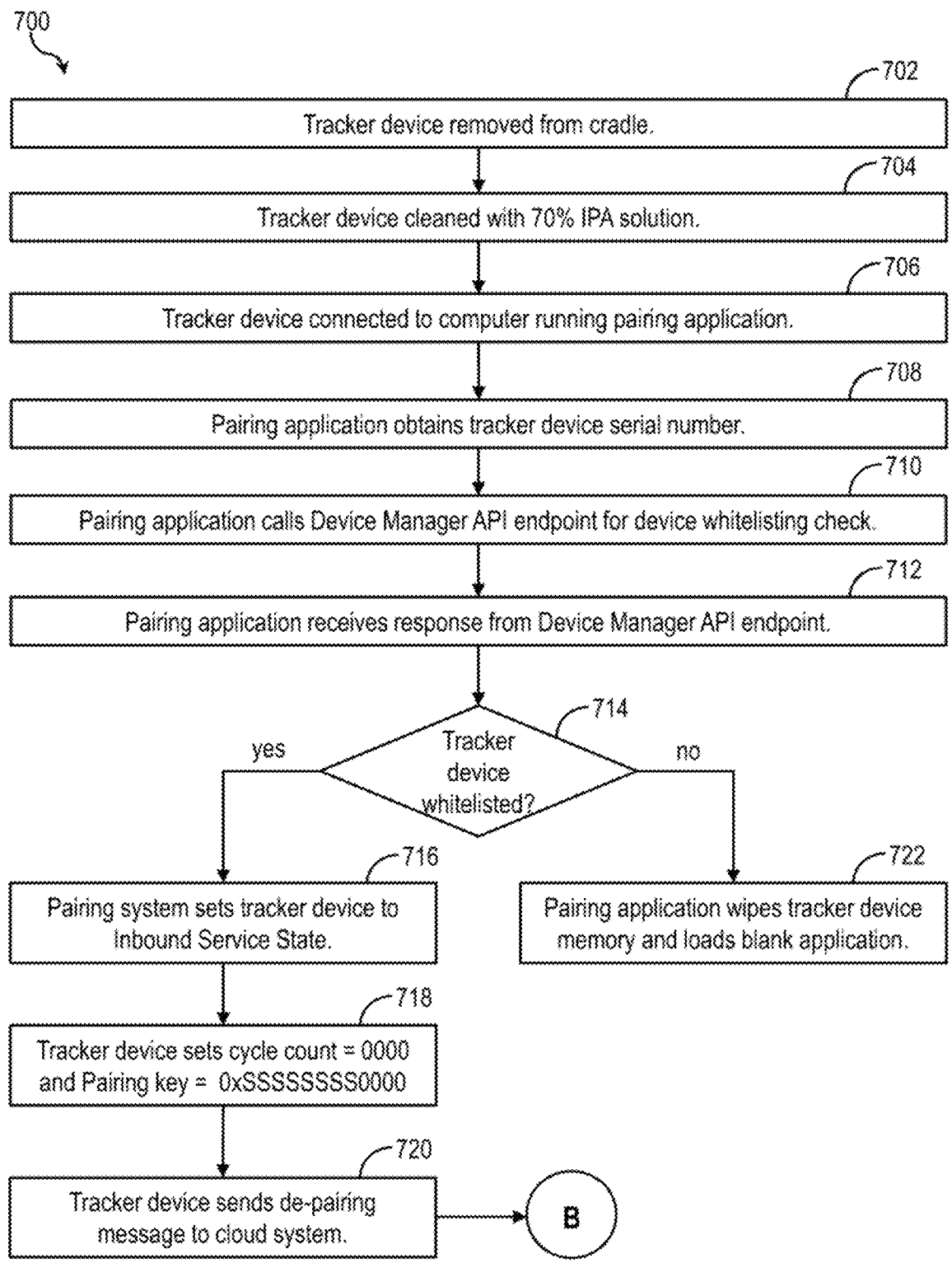
FIGS. 7A-7B is a flow chart of a unpairing process for an asset tracker, according to an embodiment.
Figure 7B:
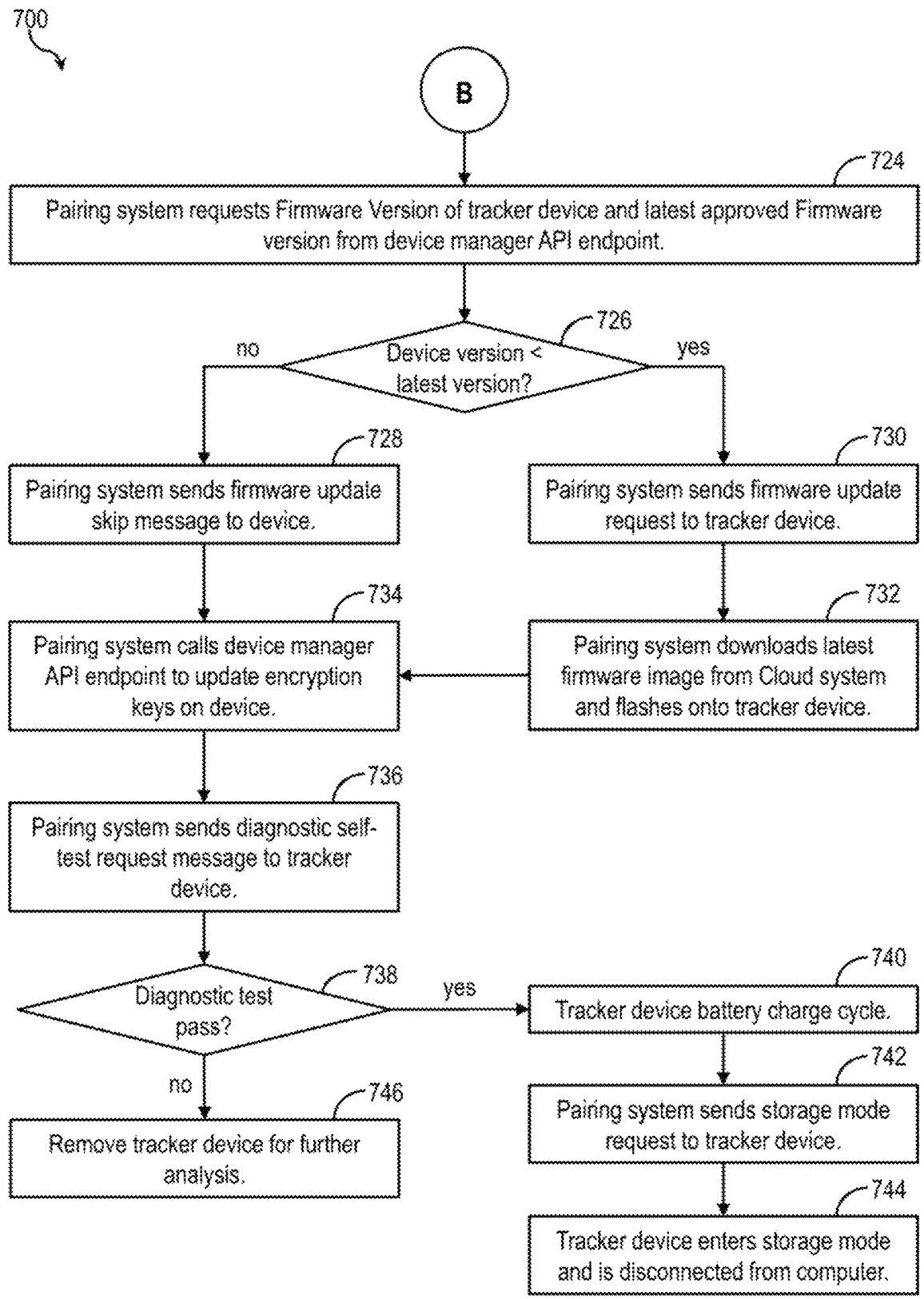
Figure 7C:
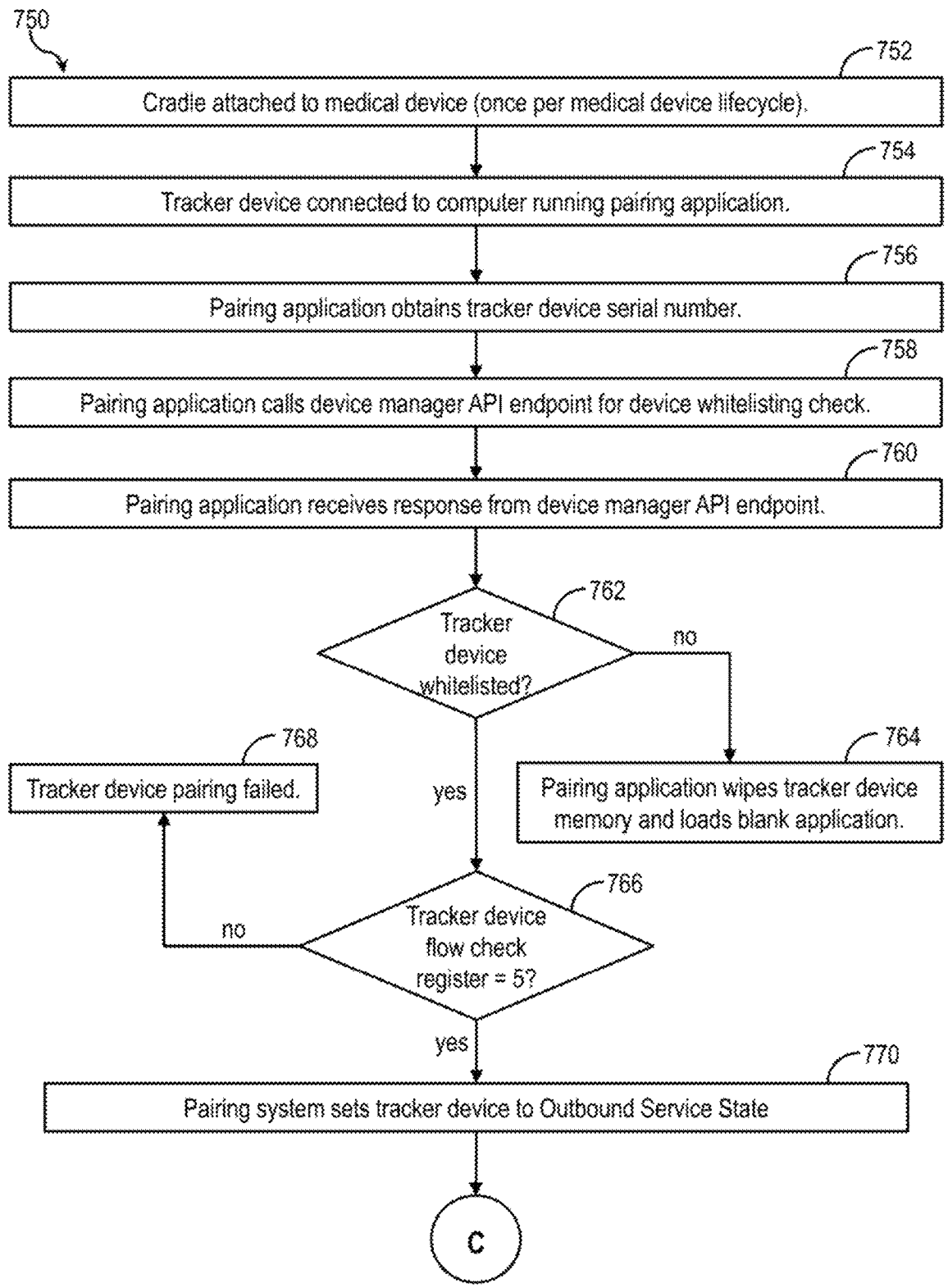
FIGS. 7C-7D is a flow chart of a pairing process for an asset tracker, according to an embodiment.
Figure 7D:
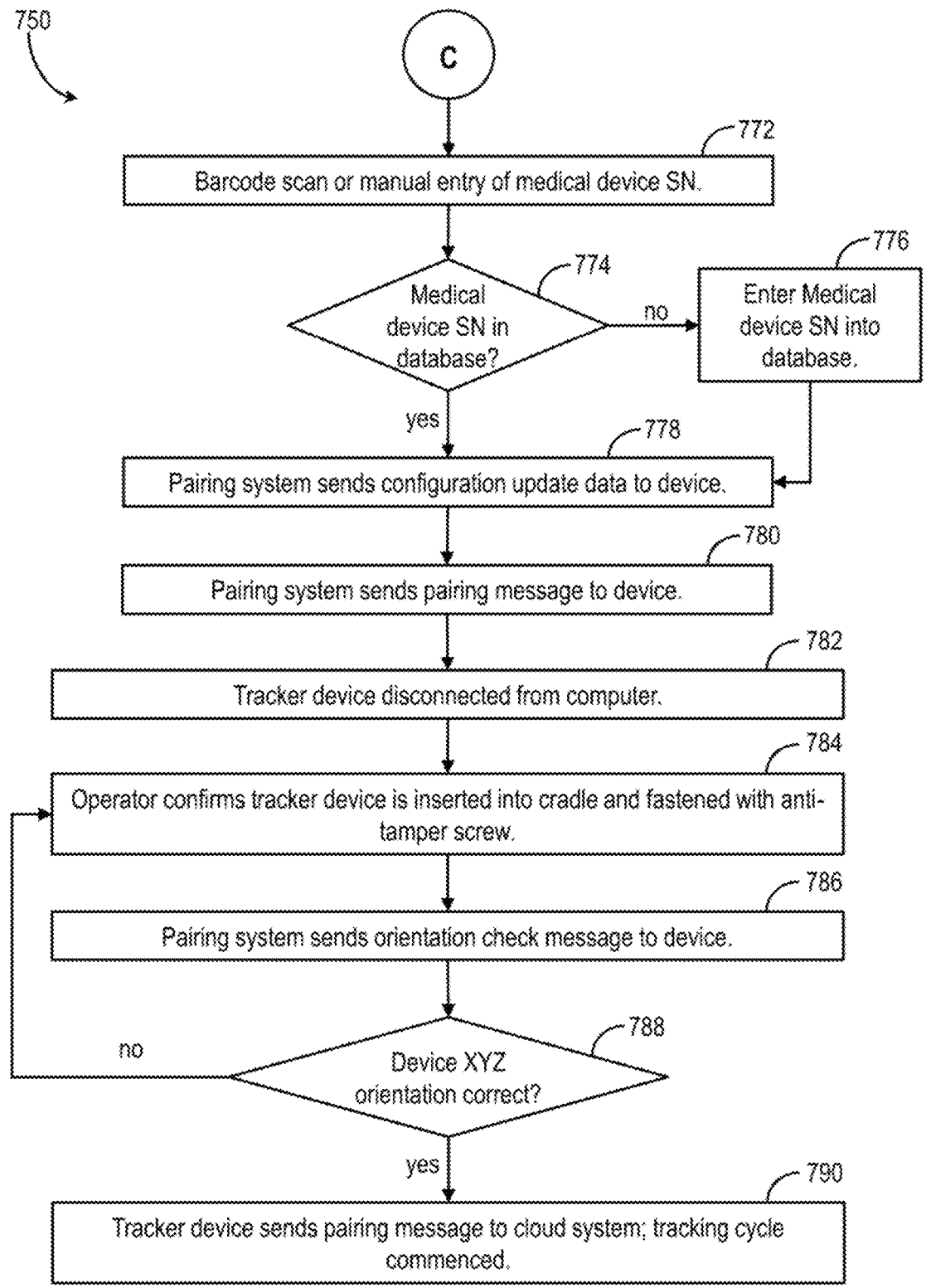

Referring to FIGS. 7A-7D, illustrated therein is a flow chart of an unpairing process 700 (FIGS. 7A-7B) and a flow chart of a pairing process 750 (FIGS. 7C-7D). The pairing processes 700, 750 may be integrated into a typical usage cycle for a medical device for tracking the medical device, recording inventory, and performing cleaning, refurbishment and recertification of the medical device, etc. The pairing processes 700, 750 may be performed by the system 170 in FIG. 1C.

Now referring to FIGS. 7A-7B illustrated therein is an unpairing process 700. The unpairing process 700 is used to physically and logically (electronically) unpair an asset tracker device from a medical device.

At 702, an asset tracker device is removed from a cradle attached to a medical device. Once the asset tracker is removed from the cradle, the cradle and/or medical device may be optionally cleaned and refurbished for next use.

At 704, the asset tracker device is cleaned by, for example, washing with a 70% solution of isopropyl alcohol (IPA). This completes the physical unpairing of the asset tracker device from the medical device.

At 706, the asset tracker device is connected via USB cable with the ID pin shorted to ground (via port 214 in FIGS. 2A-2B) to a pairing station running a pairing application.

At 708, the asset tracker device serial number is obtained by the pairing application on the pairing station through a hardware and software enumeration process, which also enables charging on the device. Hardware enumeration is completed by the tracker device detecting the logic level of the USB ID line moving to a logic low, as this line is held to a logic high through a pullup resistor to 3.3V. Software enumeration is then completed by the pairing station reading the tracker device serial number from the device and sending an enumeration signal or key that is known only to the tracker device and the cloud system. If the enumeration key is correct, the tracker device then turns on the cellular radio and sends an acknowledgement signal to the cloud system to indicate that the software enumeration process is successful.

At 710, the pairing application runs a whitelisting check for the asset tracker device by calling a device manager API endpoint in a cloud system to confirm the validity of the asset tracker device's serial number. During the device manager API endpoint call, the device manager API confirms in the cloud database if the asset tracker device has been provisioned. For example, a Boolean provisioned flag can be used and associated with each tracker device serial number. The provisioned flag is set to false after manufacturing and new entry of each unique device serial number into the database. If the tracker device is newly received from manufacturing, the device manager API completes provisioning of the device, e.g. activate cellular SIM card, etc. The Boolean provisioned flag will be set to true in the cloud database after completion of Act 710.

At 712, the pairing application receives a response, including the Boolean provisioned flag from the device manager API endpoint.

If at 714, the tracker device is not whitelisted, or has an invalid serial number, the tracker device memory is wiped and a blank application is loaded via the USB data link at 722. The failed tracker device is removed for assessment/refurbishment and the method 700 concludes. If at 714, the tracker device is determined to be whitelisted (i.e. Boolean flag is set to true), the method 700 proceeds.

At 716, the pairing application communicates with the device to set the tracker device to an inbound service state.

At 718, the tracker device updates the pairing key (sets to 8-digit device serial number+4 zeros, i.e. pairing Key=0xSSSSSSSS0000) and stores in memory.

At 720 the tracker device sends a de-pairing message to the cloud system via cellular link where the device information including pairing status will be updated in the database. The tracker device sets a flow check value to flow Check=0 and stores in memory. The tracker device enables battery charging to allow for the tracker device to be charged while it is connected to the pairing station via the USB.

At 724, the pairing application communicates with the tracker device to retrieve the current application firmware version, product ID, and hardware version of asset tracker device. The pairing application communicates to the cloud system to determine the appropriate firmware version based on the product ID and hardware version of the tracker device.

At 726, the pairing application determines whether the tracker device firmware version is less than the latest approved firmware version available for the tracker device. If at 724, the tracker device firmware version is less than the latest firmware version, a firmware update is required.

At 730 the pairing application sends a firmware update request to the tracker device, and the tracker device sets the flow check register value to flow Check=flow Check+1.

At 732, the pairing application downloads the latest firmware image from the cloud system and flashes the latest firmware into the tracker device memory. The firmware is flashed using the USB data link and then deleted off the pairing station running pairing application.

If at 724, the tracker device firmware version is not less (i.e. equal to) the latest available firmware version, then no firmware update is required and the tracker device sets the flow check value to flow Check=flow Check+2, and the pairing application sends a firmware update skip message to the tracker device at 728.

At 734, the device manager API endpoint is called by the pairing application to retrieve new encryption keys for the tracker device. The new encryption keys are encrypted by the device manager API endpoint using the current encryption keys on the tracker device. The encryption keys are known only to the tracker device and the cloud system. The pairing application sends the new encryption keys to the tracker device. The tracker device receives the encrypted version of new keys and decrypts using the current encryption keys. The tracker device stores the new encryption keys into memory and sets the flow check register value to flow Check=flow Check+1.

At 736, pairing application communicates to the device that a diagnostic self-test is required. The asset tracker device performs a diagnostic self-test of all systems and communicates the results back to the pairing application.

If at 738, the diagnostic self-test is failed, the pairing application indicates a failure mode and the failed tracker device is removed for further evaluation. The asset tracker device stores the current value of the flow check register into memory.

If at 738, the diagnostic self-test has passed, the asset tracker device sets the flow check register to flowCheck=flowCheck+1.

At 740, following a successful diagnostic test, the tracker device enters a battery charge cycle and the internal secondary battery of the tracker device is fully charged via the USB link (via the USB port 214 in FIG. 2A-2B).

At 742, once the battery is fully charged, the pairing application communicates to the tracker device to go into storage mode. In storage mode, the main rechargeable battery of the tracker device is electrically disconnected to eliminate all current load from the main battery. This step is done to ensure that maximal charge is available in the battery for the next usage cycle. Prior to entering storage mode, the tracker device sets the flow check register to flowCheck=flowCheck+1.

At 744, the tracker device enters storage mode and is disconnected from the pairing station. The tracker device may then be checked into inventory for its next usage cycle.

Now referring to FIGS. 7C-7D, illustrated therein is a pairing process 750. The pairing process 750 is used to physically and logically (electronically) pair an asset tracker device to a medical device.

At 752, a cradle is attached to a medical device. Act 752 may only be performed once for each unique medical device serial number.

At 754, a tracker device is connected to a pairing station running a pairing application by a USB cable with the ID pin shorted to ground.

At 756, the asset tracker device serial number is obtained by the pairing application on the pairing station through a hardware and software enumeration process in the same manner as described above at act 708 (FIG. 7A).

At 758, the pairing application runs a whitelisting check for the asset tracker device by calling a device manager API endpoint in a cloud system to confirm the validity of the asset tracker device's serial number. During the device manager API endpoint call, the device manager API confirms in the cloud database if the asset tracker device has been provisioned.

At 760, the pairing application receives a response from the device manager API endpoint.

If at 762, the tracker device is not whitelisted, or has an invalid serial number, the tracker device memory is wiped and a blank application is loaded via the USB data link at 764. The failed tracker device is removed for assessment/refurbishment and the method 700 concludes. If at 762, the tracker device is determined to be whitelisted, the method 750 proceeds.

At 766, the pairing application confirms if the asset tracker device has successfully completed all pairing operations (i.e. Acts 724, 734, 736, 742 in pairing method 700) to ensure proper process flow control of the pairing system. The pairing application communicates with the tracker device to retrieve current flow check register of the asset tracker device. As noted above, the flow check register of the device is incremented for each successful operation in both the pairing and unpairing methods. If flowCheck=5, then all pairing steps have been successfully completed. If not, a failure mode on the pairing application is indicated until the failed device is removed from station at 768.

At 770, the paring application communicates with the tracker device to move the tracker device into the outbound service state and set the flow check register to flowCheck=flowCheck+1.

At 772, a barcode scanner is used to read the serial number from a medical device. According to an embodiment, the medical device serial number may be manually entered into the pairing application by an operator using an input device, for example a keyboard, attached to the pairing station.

At 774, pairing application calls the device manager API endpoint in the cloud system to confirm the validity of the medical device's serial number and also the medical device type and the number of previously completed and tracked usage cycles of the medical device.

If, at 774 the medical device serial number does not exist, the method 750 proceeds to 776.

At 776, the medical device type and medical device serial number is received by the pairing application as manually entered by an operator. The pairing application calls the device manager API endpoint to enter the medical device serial number, medical device type and a medical device cycle count=0, into the cloud database.

At 778, once the medical device information is acquired, the pairing application sends configuration update data to the tracker device. The configuration data is based on the medical device type that the tracker device is to be paired to. The configuration data may include: LPS operation frequency in static and motion-based events; idle wake/sleep periods; motion detection and motion-based parameters; and thresholds including motion thresholds and therapy detection thresholds. The asset tracker device sets flow the check register to flowCheck=flowCheck+1.

At 780, the pairing application communicates to the tracker device the medical device type, medical device serial number, medical device cycle count and a 3D space XYZ orientation of asset tracker mounting.

The tracker device retrieves the hex 4-digit tracker device cycle count from memory, sets the tracker device cycle count as Cycle Count=Cycle Count+1 and stores the new value into memory. The asset tracker device then constructs a new pairing key by concatenating the 8 digit hex tracker device serial number (0xSSSSSSSS) and the updated value of the 4-digit hex Cycle Count (0xNNNN) to form the new pairing key, i.e. pairing Key=0xSSSSSSSSNNNN. The tracker device sets the flow check register to flow Check=flowCheck+1. The tracker device constructs a pairing message including the pairing key.

At 782, the tracker device is disconnected from the USB cable connection to the pairing station.

At 784 the tacker device is mated to a cradle on the medical device, by the operator, and secured in place using a tamper proof fastener. This step completes physical pairing of the tracker device and the medical device. The operator confirms in the pairing application that the tracker device is fully seated into the cradle and mechanically attached with the fastener.

At 786, the pair application software communicates wirelessly to the tracker device via the device manager API endpoint in the cloud system to request its XYZ orientation in 3D space. The asset tracker device confirms its orientation using its IMU sensor integrated circuit (IC) and confirms the 3D space XYZ orientation against the expected result.

If at 788, the 3D space XYZ orientation is incorrect, the pairing application displays a "process step failure" to the operator and a notification to correct/retry or cancel. At this point the method may revert to act 784 if the operator chooses to retry.

If at 788, the 3D space XYZ orientation is correct, the tracker device sets the flow check register to flowCheck=flowCheck+1.

At 790, the tracker device sends the pairing message constructed at Act 780 to the cloud system. The pairing application communicates wirelessly to the tracker device via the device manager API endpoint to send a pairing success message to the asset tracker device. The tracker device disables battery charging, to prevent against improper battery charging during field operation as both a safety measure and prevent against possible tampering by unauthorized individuals. The tracker device sends the pairing message, previously constructed at act 780, to the cloud system via the cellular link where the new pairing information will be stored and updated into the database. Following 790, the asset tracking cycle is commenced.

Referring to FIG. 9A, there may be operational states during which the asset tracker device cannot use RF communication. One such state may be when the medical device being tracked is in use and therapy is detected. Thus, it is desirable for some direct communication from the medical device to the asset tracker device that would let the asset tracker device know when therapy delivery is in process. This communication signaling could be used to allow the asset tracker device to perform radio operations when there is no therapy active. Generally, such an approach would require alternation to the medical device itself, which is not practical, and would require regulatory approval.

Certain medical devices use pumps and motors in their delivery of the therapy. When in operation, this class of medical devices require a motor to power the pumps that deliver the liquid-based therapies. Examples include Automated Peritoneal Dialysis, Hemo Dialysis, and infusion pumps.

When the pump and electric motor of the medical device are in operation, it is possible to externally measure the magnetic field signature of the medical device through a magnetometer sensor as illustrated in FIG. 17. However, the measured external magnetic field signal levels are typically small compared to other electronic devices such as laptop computers. The medical device may be a surgical cutter, a surgical smoke evacuator, or a pacemaker programmer. While the pacemaker programmer does not use pumps or motors, the pacemaker programmer will generates a magnetic field signature during operation that is detected using the methods disclosed herein.

While the exact construction of the pump/motor are unknown, from the Biot-Savart Law, it is assumed that the magnetic field intensity generated by the medical device will be inversely proportional to a function of distance. Therefore, since the magnetic field levels produced by these class of medical devices are typically small, it is important that the magnetometer sensor is placed as close in proximity to the medical device's surface as possible.

Additionally, another characteristic observed is that these medical devices produce a changing magnetic field over time when they are in operation. When these medical devices are not in operation, the profile of the magnetic field generated is flat and unchanging.

The changing magnetic field, which is indicative of medical device operation, can be captured by sampling the magnetometer sensor at a sufficiently high frequency, which we can define as $f_{td}$.

To capture the changing magnetic field, we shall group a set of magnetometer samples k, which are sampled at frequency $f_{td}$, into one set. We can construct the notion of multiple sequential sets in time as follows:

$$Set_1: \begin{cases} \text{magnetometer sample } 1_1 \\ \vdots \\ \text{magnetometer sample } k_1 \end{cases}$$

$$\vdots$$

$$Set_n: \begin{cases} \text{magnetometer sample } 1_n \\ \vdots \\ \text{magnetometer sample } k_n \end{cases}$$

Where each magnetometer sensor sample comprises of the magnetic field in the x-direction, the magnetic field in the y-direction, the magnetic field in the z-direction, and the magnetic field magnitude. For the i-th sample within the j-th set, an individual magnetometer sensor sample can be expressed as the following tuple:

$$\left(B_{x_i}^j, B_{y_i}^j, B_{z_i}^j, |B|_i^j\right)$$

This set construction allows us to perform mathematical operations within each set and to mathematically compare sequential sets. Within each sample set, we can mathematically determine the following elements. For the j-th set we have the following:

$$B_{x_{max}}^j = \max\left(B_{x_1}^j, B_{x_2}^j, \ldots, B_{x_k}^j\right)$$

$$B_{x_{min}}^j = \min\left(B_{x_1}^j, B_{x_2}^j, \ldots, B_{x_k}^j\right)$$

$$B_{y_{max}}^j = \max\left(B_{y_1}^j, B_{y_2}^j, \ldots, B_{y_k}^j\right)$$

$$B_{y_{min}}^j = \min\left(B_{y_1}^j, B_{y_2}^j, \ldots, B_{y_k}^j\right)$$

$$B_{z_{max}}^j = \max\left(B_{z_1}^j, B_{z_2}^j, \ldots, B_{z_k}^j\right)$$

$$B_{z_{min}}^j = \min\left(B_{z_1}^j, B_{z_2}^j, \ldots, B_{z_k}^j\right)$$

$$|B|_{max}^j = \max\left(|B|_1^j, |B|_2^j, \ldots, |B|_k^j\right)$$

$$|B|_{min}^j = \min\left(|B|_1^j, |B|_2^j, \ldots, |B|_k^j\right)$$

Where the magnetic field magnitude $|B|_j^k$, for a sample at time step k in the j-th set is defined as follows:

$$|B|_k^j = \sqrt{\left(B_{x_k}^j\right)^2 + \left(B_{y_k}^j\right)^2 + \left(B_{z_k}^j\right)^2}$$

To determine if a changing magnetic field exists, which would indicate device operation, the following trigger elements are constructed for each set:

a magnetic field delta (referred to herein as Trigger Element #1):

$$|B|_{max}^j - |B|_{min}^j \geq \gamma_1$$

a magnetic field delta square (referred to herein as Trigger Element #2):

$$\left(B^j_{x_{max}} - B^j_{x_{min}}\right)^2 + \left(B^j_{y_{max}} - B^j_{y_{min}}\right)^2 + \left(B^j_{z_{max}} - B^j_{z_{min}}\right)^2 \geq \gamma_2$$

If either of the trigger elements is greater than the thresholds $\gamma_1$, $\gamma_2$, than it is assumed that a phenomenon consistent with medical device operation has been observed. The first trigger element relates to capturing and identifying if a change in the magnetic field magnitude within a set exists. The second element relates to capturing and identifying if a change in one of the 3D space magnetic field vectors exist.

Between adjacent sets j and (j−1), we can calculate if a large change in magnetic field was observed by using the following:
a magnetic field time delta (referred to herein as Trigger Element #3):

$$\left(|B|^j_{max} - |B|^j_{min}\right) - \left(|B|^{j-1}_{max} - |B|^{j-1}_{min}\right) \geq \gamma_3$$

If the trigger element is greater than the thresholds $\gamma_3$, than it is assumed that a phenomenon consistent with medical device operation has been observed. This trigger element relates to capturing and identifying if a large change in the magnetic field magnitude between set exists, e.g. consistent with events such as turning on or off.

At a high level, it can be stated that a therapy and medical device operation has been detected by the asset tracker device if any of the above three trigger element conditions have been met, i.e.

Trigger Element #1 $\geq \gamma_1$

Trigger Element #2 $\geq \gamma_2$

Trigger Element #3 $\geq \gamma_3$ where $\gamma_1$, $\gamma_2$, and $\gamma_3$ are the threshold levels that are predetermined for each medical device type based on a certain mounting position of the asset tracker device.

The above threshold levels for the algorithm are unique for each different medical device. The threshold levels defined are a function of the magnetic field signature of the medical device and also of the magnetometer sensor IC location and its distance to the surface of the medical device. The unique threshold levels are programmed into the asset tracker device at time of pairing system process with the medical device (FIGS. 7C-7D).

An implementation approach for this therapy detection method would be to continuously sample the magnetometer and determine if any of the trigger elements conditions have been met. Continuous sampling, while accurate, would impact the battery life of the device. Another approach would be to implement sleep and wake cycles that would allow the device to go into a low power state for most of its lifecycle. During the wake cycle, a magnetometer set would be sampled and the trigger element conditions would be checked. The duration of the sleep cycle is variable and is dependent on the medical device magnetic profile generated during a therapy.

According to an embodiment, the medical therapy detection method may be modified to include vibration detection as another indicator of medical device usage. It has been observed that low level vibrations can be reliably measured from the medical device during delivery of therapies. The challenge is to distinguish transport motion from therapy events.

One possible approach would be to use an IMU sensor IC, which provides for both an accelerometer and gyroscope. Probabilistically speaking, when motion occurs, changes in both the 3-axis acceleration (Ax, Ay, Az) measured by the accelerometer and 3-axis angular position rate of change (Gx, Gy, Gz) as measured by the gyroscope should be observed. Over longer periods of time, it is statistically unlikely to see cases of motion without any changes to the angular position.

For cases when a medical device therapy is being delivered, the pump/motor of the medical device will produce vibrations that can be observed as a changing force that is measurable by the accelerometer. However, there will be minimal changes in the angular position (roll, pitch, and yaw) as observed by the gyroscope.

Considering the same sample set framework as from before, we could group a set IMU IC samples k, which are sampled at frequency $f_{td}$, into one set. We can construct the notion of multiple sequential sets in time as follows:

$$IMU\ Set_1: \begin{cases} IMU\ \text{sample}\ 1_1 \\ \vdots \\ IMU\ \text{sample}\ k_1 \end{cases}$$

$$\vdots$$

$$IMU\ Set_n: \begin{cases} IMU\ \text{sample}\ 1_n \\ \vdots \\ IMU\ \text{sample}\ k_n \end{cases}$$

Where each sample comprises of the acceleration in the x-direction, the acceleration in the y-direction, the acceleration in the y-direction, the acceleration in the z-direction, the angular rate of change on the x-axis, the angular rate of change on the y-axis, and the angular rate of change on the z-axis. For the i-th sample within the j-th set, an IMU sample can be expressed as the following tuple:

$$\left(A^j_{x_i}, A^j_{y_i}, A^j_{z_i}, G^j_{x_i}, G^j_{y_i}, G^j_{z_i}\right)$$

This set construction allows us to perform mathematical operations within each set and to mathematically compare sequential sets as previously stated. Within each sample set, we can mathematically determine the following elements. For the j-th set we have the following new elements:

$$A^j_{x_{max}} = \max\left(A^j_{x_1}, A^j_{x_2}, \ldots, A^j_{x_k}\right)$$

$$A^j_{x_{min}} = \min\left(A^j_{x_1}, A^j_{x_2}, \ldots, A^j_{x_k}\right)$$

$$\Delta A^j_x = \left|A^j_{x_{max}} - A^j_{x_{min}}\right|$$

$$A^j_{y_{max}} = \max\left(A^j_{y_1}, A^j_{y_2}, \ldots, A^j_{y_k}\right)$$

$$A^j_{y_{min}} = \min\left(A^j_{y_1}, A^j_{y_2}, \ldots, A^j_{y_k}\right)$$

$$\Delta A^j_y = \left|A^j_{y_{max}} - A^j_{y_{min}}\right|$$

$$A^j_{z_{max}} = \max\left(A^j_{z_1}, A^j_{z_2}, \ldots, A^j_{z_k}\right)$$

$$A^j_{z_{min}} = \min\left(A^j_{z_1}, A^j_{z_2}, \ldots, A^j_{z_k}\right)$$

-continued $$\Delta A_z^j = |A_{z_{max}}^j - A_{z_{min}}^j|$$

$$G_{x_{max}}^j = \max(G_{x_1}^j, G_{x_2}^j, \ldots, G_{x_k}^j)$$

$$G_{x_{min}}^j = \min(G_{x_1}^j, G_{x_2}^j, \ldots, G_{x_k}^j)$$

$$\Delta G_x^j = |G_{x_{max}}^j - G_{x_{min}}^j|$$

$$G_{y_{max}}^j = \max(G_{y_1}^j, G_{y_2}^j, \ldots, G_{y_k}^j)$$

$$G_{y_{min}}^j = \min(G_{y_1}^j, G_{y_2}^j, \ldots, G_{y_k}^j)$$

$$\Delta G_y^j = |G_{y_{max}}^j - G_{y_{min}}^j|$$

$$G_{z_{max}}^j = \max(G_{z_1}^j, G_{z_2}^j, \ldots, G_{z_k}^j)$$

$$G_{z_{min}}^j = \min(G_{z_1}^j, G_{z_2}^j, \ldots, G_{z_k}^j)$$

$$G_z^j = |G_{z_{max}}^j - G_{z_{min}}^j|$$

These measurements could be added as an additional trigger element for vibration without motion. This trigger element would check for vibrational forces by measuring change in acceleration against a threshold. Lack of motion would be confirmed through a minimal level of rotational change by measuring change in angular position against a threshold.

In order to create a suitable vibration-based trigger element, it is noted that a single instance from a sample set will not be sufficient to determine vibration without motion. As previously stated, it is over a longer time-period where the determination can be made.

For each sample set, we can make the following calculation:

$$\Delta A_x^j + \Delta A_y^j + \Delta A_z^j \geq \gamma_4$$

$$\Delta G_x^j + \Delta G_y^j + \Delta G_z^j \leq \gamma_5$$

If both of the above expressions are true, i.e. acceleration over a threshold and change of angular position under a threshold, then we can increment a vibration counter, i.e. set vibrationCntr=vibrationCntr+1.

We can then state that vibration due to a medical device therapy operation would be observed if we exceed a certain threshold as an observed vibration (referred to herein as Trigger Element #4):

$$vibrationCntr \geq \gamma_6$$

It is noted that the threshold levels $\gamma_4$, $\gamma_5$, and $\gamma_6$ will be based on the type of medical device used. The number of sample sets and observed instances of threshold depend on the type of therapy and medical device type. This fourth trigger element can be easily fused/added into the therapy detection algorithms noted above wherever the trigger elements are used, i.e., in heuristic window monitoring and pre-LPS therapy detection.

One possible approach for implementation of this trigger element would be synchronize both the magnetometer and IMU so that they are grouped in common sample and sample sets. For the i-th sample within the j-th set, an individual magnetometer sensor and IMU sample can be expressed as the following tuple:

$$(B_{x_i}^j, B_{y_i}^j, B_{z_i}^j, |B|_i^j, A_{x_i}^j, A_{y_i}^j, A_{z_i}^j, G_{x_i}^j, G_{y_i}^j, G_{z_i}^j)$$

This allows for therapy detection which could be used in both the heuristic window operation and pre-LPS therapy detection check, where the magnetometer sensor IC and IMU sensor IC is sampled at frequency $f_{td}$ with k samples per set and j sets. According to an embodiment, $f_{td}>10$ Hz; k samples can range between 10 and 50; j sets can range between 1 to 25. The exact values of parameters and threshold levels, including $f_{td}$, j and k are a function of the medical device type.

From this, it can be stated that a therapy and medical device operation has been detected by the asset tracker device if any of the four trigger element conditions have been met, i.e.

Trigger Element #1 $\geq \gamma_1$

Trigger Element #2 $\geq \gamma_2$

Trigger Element #3 $\geq \gamma_3$

Trigger Element #4 $\geq \gamma_6$

Another possible approach would be to leverage the first-in-first-out queue capability of many modern IMU ICs. These ICs implement a functionality that allows for IMU sampling and storage into the IMU IC while the microcontroller is in a deep sleep mode. This approach would result in a lengthy vibrational check via the IMU while the asset tracker device is in deep sleep and a relatively short magnetometer check when the device awakens from deep sleep and enters the idle wakeup period.

This approach will result in two distinct sample sets that can be logically grouped as follows:

$$(A_{x_i}^j, A_{y_i}^j, A_{z_i}^j, G_{x_i}^j, G_{y_i}^j, G_{z_i}^j)$$

$$(B_{x_i}^j, B_{y_i}^j, B_{z_i}^j, |B|_i^j)$$

From this, therapy detection can be achieved by sampling the magnetometer sensor IC at frequency $f_{td-magnetometer}$ with k samples per set and j sets. Typically, $f_{td}>10$ Hz; k samples can range between 10 and 50; j sets can range between 1 to 5. The exact values of parameters are a function of the medical device type.

The IMU sensor IC samples frequency $f_{td-imu}$ with n samples per set and j sets per cycle. Thus, a therapy and medical device operation has been detected by the asset tracker device if any of the four trigger element conditions above have been met. As such, the asset tracker device can be used to detect different medical devices containing pumps or motors.

It should be noted that vibration events need to be triggered over a series of wakeup cycles. The multiple wakeup cycles and longer time-period are needed since physical interaction by the patient with the medical device may cause micro-events, which may be a false trigger.

A final approach to therapy detection by vibration would be to continuously sample the IMU for vibration and motion. As with the continuous monitoring of the magnetometer, this approach would impact the battery life of the device, but it would likely result in improved accuracy.

The ability of the asset tracker device to measure and report the frequency of medical device operation while respecting patient privacy can also be leveraged to ensure the patient regularly completes their required medical therapy and track therapy utilization of an entire fleet of medical devices.

To effectively prevent asset tracker device cellular operations (which creates a power profile that exceeds medical device certification) while the medical device is delivering therapy it is necessary to: (1) create a heuristic window based on device measurements for a time window during the day when medical device therapy is not typically delivered, and therefore it is likely safe to perform cellular operations (FIGS. 8A-8B); and (2) create an method that confirms no medical device operation prior to a planned device cellular operation.

The heuristic window is created to reduce the chance of collision between a planned device cellular operation and therapy being delivered by the medical device. Therefore, frequent monitoring operation by the device is required to construct time windows when likely therapy is being delivered by the medical device.

Additionally, many medical devices have common usage patterns. For instance, in Automated Peritoneal Dialysis therapy, patients usually have the therapy delivered at night when they are sleeping. Other therapies such as infusion pumps may have the patient deliver the therapy during the day when they are awake.

A priori knowledge of the medical device type can be known to the asset tracker device through the pairing system process (FIGS. 7C-7D). Therefore, a priori knowledge can be used to construct a baseline heuristic time window as the initial condition for the medical device type being tracked by the asset tracker device. From the initial condition, this window can be modified based upon the continual measurements of the asset tracker device operation.

Figure 8A:
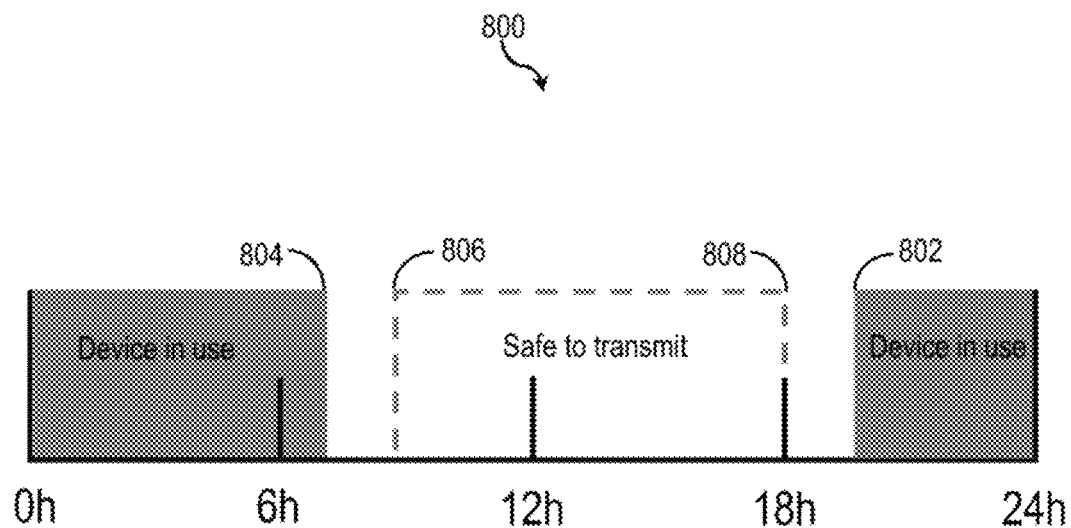
FIGS. 8A-8B are diagrams of exemplary heuristic safe transmit windows, according to several embodiments.
Figure 8B:
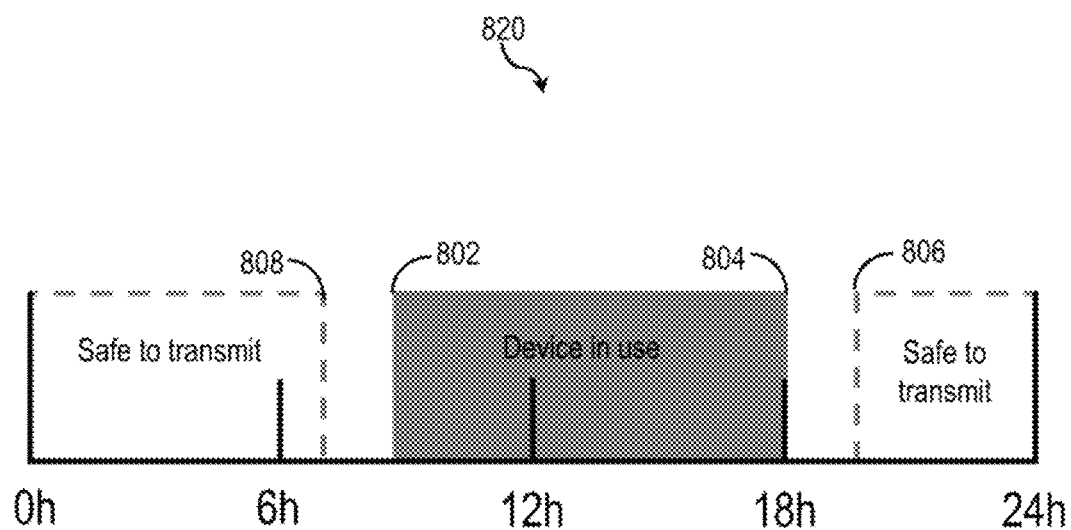

Now referring to FIGS. 8A-8B, illustrated therein is a diagram of heuristic time windows 800, 820 according to several embodiments. FIG. 8A illustrates a heuristic window 800 when a therapy is typically delivered over midnight relative to local time of the device; FIG. 8B illustrates a heuristic window 820 when the therapy is typically delivered during the day relative to local time of the device.

The heuristic windows 800, 820 include four times, which are stored in the device memory as integers representing the number of minutes elapsed from 00:00 local time up until 23:59 local time: a likely therapy start time 802, a likely therapy end time 804, a likely safe transmit start time 806 and a likely safe transmit end time 808. Each of the times 802, 804, 806, 808 have a value between 0 and 1440, corresponding to a minute between 00:00 and 23:59.

Prior to a planned cellular operation by the asset tracker device, an algorithmic therapy detection check is required to ensure that no medical device operation is occurring. In this case as well, a priori information can be used to determine the algorithm framework.

For example, in Automated Peritoneal Dialysis machines, there is a standard cycle of drain, fill, and dwell. A Peritoneal Dialysis therapy consists of typically three to five of these standard cycles. In the drain and fill portions of the cycle, the pump/motor of the dialysis machine is in constant operation, as it is performing fluid exchange. In these cases, measurements by the magnetometer sensor will trigger all the previously indicated trigger elements.

During the dwell portion of the cycle, the pump could be off, or the pump could be in operation preparing for the next cycle. In the case when the pump is off during the dwell cycle, none of the trigger elements would be satisfied, as is expected.

Therefore, the issue arises that a therapy detection check for Automated Peritoneal Dialysis medical devices prior to a planned cellular operation should cover a sufficient time-period so that a false negative is not generated during the dwell portion of the therapy cycle. A false negative in this instance would allow for the asset tracker device to erroneously perform cellular operations. Thus, for this class of medical devices knowledge of the therapy including cycle length and dwell length can be used to devise the framework of the algorithm.

For example, in infusion pumps the device is generally on and delivering a therapy or it is off. When the therapy is being delivered, the pump/motor will also be on. Therefore, a therapy detection check for infusion pump medical devices prior to planned cellular operations by the medical device may comprise of a constant duration check prior to performing cellular operations.

To implement the asset tracker device heuristic window and medical therapy pre-check aspects of the present invention, a real-time clock, microcontroller with external flash memory, a magnetometer sensor IC, and a cellular radio is required for the asset tracker device. The magnetometer sensor IC is required to be placed as close to the surface of the medical device within the asset tracker enclosure as is possible.

The real-time clock tracks time in Unix or Epoch time, which is the number of seconds elapsed since 12:00 am Jan. 1, 1970 UTC. The real-time clock is synchronized and kept accurate each time the cellular radio is powered and connected to the cellular network. Based on the configuration of the device, the next planned transmission time to the cloud-based system is also stored into flash memory. The asset tracker will spend most of its time in a deep sleep cycle to conserve power and battery life. However, there are a few circuits that are in operation such as the real-time clock circuit, which is used to track time.

As shown in FIG. 1E, the tracker device is either in an idle low power state 134 or an active LPS state 136. During the idle low power state 134, the device conserves battery power and measures its environment with the suite of onboard sensors. During the active LPS state 136, the device performs an LPS and performs cellular operations communicating with the cloud system.

During the idle low power state 134, the device implements planned wake-up cycles ranging anywhere between once every minute to once every hour depending on the unique device configuration assigned during the pairing process (FIGS. 7A-7D) or modified by the adaptive control system (FIGS. 3A-5B).

Now referring to FIG. 9A, illustrated therein is a flow chart of an idle low power operational state 900 for the asset tracker device. For brevity and ease of illustration, the key steps are described. During an idle wakeup cycle (902) the following set of operations may be performed by the asset tracker device.

If the present time is greater than the next planned transmission time (904), the device starts therapy pre-checks (906), and changes state to LPS. Depending on type of medical device, pre-check may start 1-2 hours prior to a planned cellular operation.

If the device is in an idle static state, a motion detection check is performed (908). If motion is detected the tracker device changes its state and configuration to motion based state (910).

If the device is in an idle motion state, the device checks whether absence of motion has been detected (912). If absence of motion is detected, the device changes its state and configuration to idle based state (914).

Following the motion checks, the device performs a therapy detection check (916, 918), wherein the magnetometer sensor IC is sampled at frequency $f_{td}$ with k samples per set and j sets and the results are compared to determine if any of the trigger element conditions have been met. According to an embodiment, $f_{td}$>10 Hz; k samples can range between 10 and 50; j sets can range between 1 to 25. The exact values of parameters and threshold levels, including $f_{td}$, j and k are a function of the medical device type. The tracker device also samples all other sensors and stores the results into memory. Based on the results of the therapy detection test, the heuristic window is adjusted accordingly.

Referring again to FIGS. 8A-8B, there are two scenarios for the likely therapy window. The first scenario illustrated in FIG. 8A is when the likely therapy start time 802 is greater than the likely therapy end time 804. This corresponds to the therapy starting before midnight (0 h) and ending at some point later the next day. In this scenario a boolean flag for therapy over midnight time is set to true.

The second scenario illustrated in FIG. 8B is when the likely therapy start time 802 is less than the likely therapy end time 804 value. This corresponds to the therapy starting after midnight (0 h local time) and ending at some point later the same day. In this scenario a Boolean flag for the therapy over midnight is set to false.

Figure 9B:
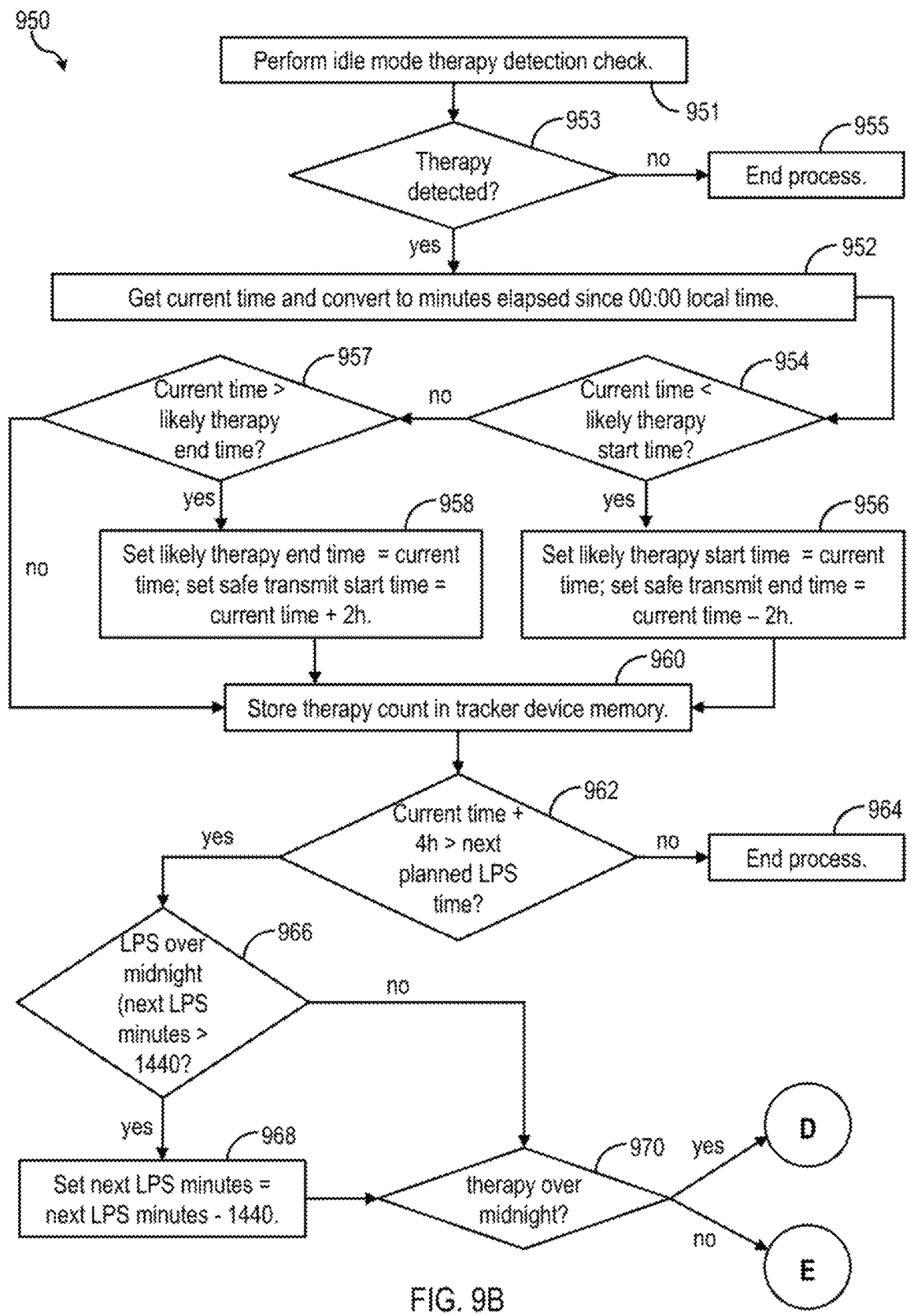
FIGS. 9B-9C is a flow chart of a method for adjusting a planned LPS operation to fit a heuristic window, according to an embodiment.
Figure 9C:
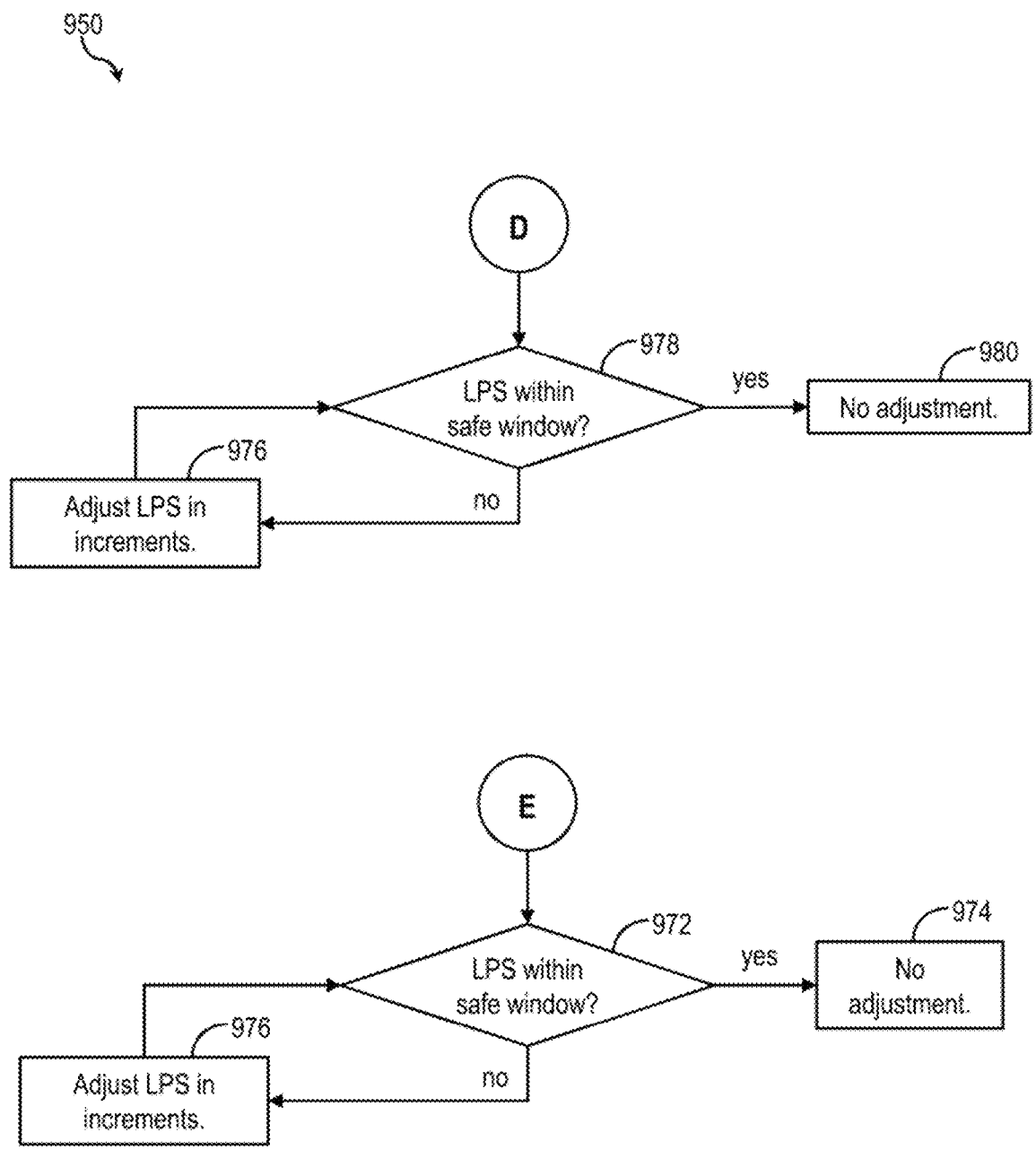

Referring to FIG. 9B, illustrated therein is a flow chart of a method 950 for adjusting a planned LPS operation to fit a heuristic window.

At 951, the asset tracker device performs an idle mode therapy detection check. If, at 953 a therapy is not detected, the method 950 concludes. The method 950 proceeds only when the therapy detection check finds an active ongoing therapy at 953.

At 952, the asset tracker device obtains the current time and converts to minutes elapsed since midnight local time (i.e., since 00:00, 24-hour clock).

If at 954, the current time is greater than a likely therapy start time, the device sets the likely therapy start time=current time, and sets a safe transmit end time=current time−2 hours.

If at 954, the current time is not greater than a likely therapy start time, the device queries whether the current time is less than the likely therapy end time (957).

If at 957, the current time is less than the likely therapy start time, the tracker device sets the likely therapy end time=current time, and sets a safe transmit start time=current time+2 hours (958).

If a therapy is detected at 953, it is possible that the therapy is already within the existing window (i.e., outcome of acts 954 and 957 are both no). It is also possible that the detected therapy occurs before the existing window. If that is the case, the window needs to be extended on the left side to account for this possibility (i.e. outcome of act 954 is yes and act 956 is performed). It is also possible that the detected therapy occurs after the existing window. If that is the case, the window needs to be extended on the right side to account for this possibility (i.e. act the outcome of act 954 is no and act 958 is performed).

At 960, a therapy count is stored in the tracker device memory. First a current hour value is determined by dividing the current time integer by 24 to result in a number between 0-24. For example, when wakeup cycles occur once per hour, the therapy count for the current hour is calculated as therapy count=therapy count+1.

At 962, the device queries whether the next planned cellular based operation, i.e. LPS will occur in the next four hours. If the current time+4 hours is not greater than the next planned LPS operation time, the method 905 concludes, at 964 with just a possible update to the heuristic window (act 956 or 958). If the next planned cellular or LPS operation is within the next four hours, the upcoming cellular/LPS operation time needs to be shifted to a safe transmit window.

Since the heuristic window reflects the local 24-hour clock and the device measures continuous epoch time, a conversion of the next planned LPS operation into a 24-hour clock is required. As the current epoch time was already previously converted into the 24-hour clock at 952, i.e. minutes elapsed since 00:00, the device subtracts the current epoch time from the next planned LPS epoch time and adds this minute value to the current 24-hour based time, i.e. number of minutes elapsed since 00:00, to set the value next LPS minutes.

At 966 the device queries whether the next planned LPS operation occurs over midnight based on the 24-hour clock. If yes, at 968 the device sets the next LPS minutes=next LPS minutes−1440.

At 970, the device queries whether safe transmit window wraps over midnight (i.e., whether the therapy does not occur over midnight and the Boolean flag therapy-overmidnight=false).

If at 970, the safe transmit window is not over midnight (FIG. 8A), and Boolean flag therapyOverMidnight=true, the tracker device queries, at 972, whether the LPS operation period is within the heuristically determined safe transmit window. That is, if the likely therapy end time (804 in FIG. 8A)≤ next LPS minutes and next LPS minutes≤likely therapy start (802 in FIG. 8A). If true, there is no adjustment to the next planned LPS operation time and the method 950 concludes at 974.

If, at 972 the LPS operation falls outside the safe transmit window, the tracker device at 976 sets a Boolean flag safetimefound=0, sets shifttoLPSTime=0 and commences to successively adjust the LPS operation period by increments of 60 minutes until the LPS operation time is within the safe transmit window.

If at 970, the safe transmit window is over midnight (FIG. 8B), and Boolean flag therapyOverMidnight=false, the tracker device queries, at 978, whether the LPS operation period is within the heuristically determined safe transmit window. That is, if likely therapy end (804 in FIG. 8B)≤ next LPS minutes≤1440 or if 0≤next LPS minutes≤likely therapy start (802 in FIG. 8B). If true, no adjustment to the next planned LPS operation time and the method 950 concludes at 980.

If at 978 LPS operation falls outside the safe transmit window, the method 950 reverts to act 976 in a loop until the LPS operation time is within the safe transmit window.

It should be restated that the heuristic window is not designed to eliminate the possibility of planned cellular operations while a medical device therapy is ongoing, but it is done to reduce the possibility of collisions based on the patterns observed.

Furthermore, the above example illustrates just one possible method for adjusting and determining the heuristic window. The above method 950 simply adjusts the window based on a single occurrence and will not account for infrequent outlier cases. Another method such as a minimum threshold count for the window boundaries could be used. Further logic could be used to filter out therapy cases done outside of the window.

Additionally, as an example for Peritoneal Dialysis, which is normally done at night, we may see medical therapies performed during the day when the patient is consulting with a doctor or nurse. Considering this possibility, a heuristic window could be constructed based on a probabilistic distribution of observed therapies. Yet another method to construct a heuristics window could be to consider only last number of finite days, e.g., ten, to construct the rules for the window.

The above approaches detail possible methods for implementing a low power heuristic window check on an asset tracker device. It is noted that it is possible that the device could be kept in an idle state with continuous monitoring and not ever go into deep sleep to conserve power. This approach will result in a lower device battery life, but this approach would negate the need for a therapy detection check since there is continuous monitoring.

Now turning to the situation when the tracker device is in an active LPS state, the device performs an LPS and performs cellular operations communicating with the cloud system. However, prior to running the LPS operation, a therapy detection check is required. The sequence of operations in the LPS state are: 1. Pre-LPS therapy detection check; 2. if therapy detected, adjust planned LPS time and return to idle state; 3. If no therapy detected commence LPS operation including turning on cellular radio; 5. Location API endpoint call (FIG. 5A-5B); 6. Message API endpoint call (FIG. FIG. 3D); 7. Wait one minute; and 7. Message ACK API endpoint call (FIG. 4B).

For the pre-LPS therapy detection check, as previously noted, the duration of the detection check is a function of the type of medical device and the nature of the therapy. It is also a function of the sampling frequency for the heuristic window calculation. In the case of continuous monitoring, no additional therapy detection check would be required, as the continuous monitoring is the detection operation.

For the cases like Automated Peritoneal Dialysis where the dwell cycle may present false negatives, a longer detection check period is required to cover these periods where the pump/motor is off in the middle of a therapy. One example would be to continuously monitor for a period of two hours prior to the planned LPS operations. Another example would be to wake periodically using the following sequence to minimize current consumption.

This exemplary sequence is devised based on a priori knowledge of both the operation of a particular Automated Peritoneal Device and the therapy:

1. When the LPS operation is 125 minutes away, start the therapy detection cycle;
2. Therapy detection mode is run 5 times for a total of ~125 minutes. Each therapy detect run comprises 10×30 second sleep cycle+1-5 second wake cycle+20 minutes deep sleep=25 minutes. During each wake cycle the magnetometer is sampled at frequency $f_{td}$ with k samples per set and j sets. According to an embodiment, $f_{td}$>10 Hz; k samples can range between 10 and 50; j sets can range between 1 to 25. The exact values of parameters and threshold levels, including $f_{td}$, j and k are a function of the medical device type.
3. For each therapy detection run calculate therapy detection based on Trigger Elements #1, Trigger Element #2 or Trigger Element #3 as defined above. If no therapy is detected, proceed to step 4.
4. If a therapy is detected: track therapy heuristics; adjust LPS time to Next LPS hours=Next LPS time+12 hours; set tracked device state to idle mode; and go to sleep for duration based on device configuration and next state.
5. Set the device state to LPS mode and allow cellular operations.
6. Continue therapy detection during LPS mode so that cellular operations can be immediately turned off if medical device operation is detected. Sample magnetometer IC for 1 to 5 seconds at frequency $f_{td}$ with k samples per set and j sets. According to an embodiment, $f_{td}$>10 Hz; k samples can range between 10 and 50; j sets can range between 1 to 25. The exact values of parameters and threshold levels, including $f_{td}$, j and k are a function of the medical device type.
7. Calculate therapy detection based on Trigger Elements #1, Trigger Element #2 or Trigger Element #3 as defined above.

While the above description provides examples of one or more devices, methods, or systems, it will be appreciated that other devices, methods, or systems may be within the scope of the claims as interpreted by one of skill in the art.

The invention claimed is:

1. A method for detecting when a medical device is operating, the method comprising:
    sampling measurements from a magnetometer in a tracker device attached to a surface of the medical device, the magnetometer configured to detect a magnetic field emanating from at least one of a pump and a motor in the medical device; and
    determining an operational state of the medical device based on the measurements from the magnetometer.

2. The method of claim 1, further comprising:
    mounting the tracker device to the surface of the medical device.

3. The method of claim 1, wherein sampling measurements from the magnetometer comprises sampling a magnetic field in a x-direction, sampling a magnetic field in a y-direction and sampling a magnetic field in a z-direction.

4. The method of claim 1, further comprising:
    sensing a change in magnetic field strength based on the measurements from the magnetometer.

5. The method of claim 4, wherein sensing a change in the magnetic field strength comprises:
    determining whether the change in the magnetic field is greater than a predetermined threshold for the medical device.

6. The method of claim 1, further comprising:
    waking the tracker device from a low power state prior to sampling the measurements from the magnetometer; and
    returning the tracker device to the low power state after determining the operational state of the medical device.

7. The method of claim 1, further comprising:
    electronically pairing the tracker device to the medical device.

8. The method of claim 1, further comprising:
    sampling measurements from an inertial measurement unit (IMU) in the tracker device; and
    confirming the operational state of the medical device based on the measurements from the IMU.

9. The method of claim 8, wherein sampling measurements from the IMU comprises:
    recording acceleration in a x-direction, recording acceleration in a y-direction, recording acceleration in a z-direction, recording an angular rotation in the x-direction, an angular rotation in the y-direction and an angular rotation in the z-direction.

10. The method of claim 9, wherein confirming the operational state of the medical device comprises:
sensing a change in acceleration based on the measurements from the IMU.

11. The method of claim 10, wherein sensing a change in acceleration comprises:
determining whether the change in the acceleration is greater than a predetermined threshold for the medical device; and
determining whether a change in angular rotation is less than a predetermined threshold for the medical device.

12. A system for detecting when a medical device is operating, the system comprising:
a tracker device for mounting to a surface of the medical device, the tracker device comprising:
a magnetometer for detecting a magnetic field emanating from at least one of a pump and a motor in the medical device when the medical device is providing a therapy.

13. The system of claim 12, wherein the magnetometer is configured to: sample a magnetic field in a x-direction, sample a magnetic field in a y-direction and sample a magnetic field in a z-direction.

14. The system of claim 12, wherein the tracker device is configured to sense a change in magnetic field strength emanating from the medical device based on measurements from the magnetometer.

15. The system of claim 12, wherein the tracker device further comprises:
an inertial measurement unit (IMU) configured to:
measure acceleration in the x-direction, the y-direction and the z-direction; and
measure angular rotation in the x-direction, the y-direction and the z-direction.

16. The system of claim 15, wherein the tracker device is configured to sense a change in acceleration of the medical device based on measurements from the IMU.

17. The system of claim 12, further comprising:
a cradle for adhering to the medical device, the cradle comprising:
a dock for receiving the tracker device; and
a tamper proof fastener for removably attaching the tracker device to the cradle.

18. The system of claim 12, further comprising:
a pairing station comprising:
a USB interface for connecting to the tracker device and charging the tracker device; and
a scanner for reading a barcode on the asset;
wherein the pairing station is configured to:
receive a first serial number from the tracker device via the USB interface;
authenticate the tracker device based on the first serial number;
update the tracker device firmware upon authentication of the tracker device;
complete diagnostic testing of the tracker device upon authentication of the tracker device;
charge the tracker device via the USB interface upon authentication of the tracker device;
receive a second serial number from the medical device via the scanner;
provide configuration information to the tracker device based on a medical device type; and
associate the first serial number and the second serial number to a pairing key, wherein the pairing key logically pairs the tracker device to the medical device.

19. A medical device comprising:
at least one of a pump and a motor; and
a tracker device on a surface of the medical device, the tracker device comprising a magnetometer for detecting a magnetic field emanating from the pump and/or the motor medical device when the medical device is providing a therapy.

* * * * *